(12) United States Patent
Wieland et al.

(10) Patent No.: US 10,893,982 B2
(45) Date of Patent: Jan. 19, 2021

(54) PERFORATED, LAYERED WOUND TREATMENT MATERIAL

(75) Inventors: Martin Wieland, Coesfled (DE); Antje Grill, Münster (DE)

(73) Assignee: MEDSKIN SOLUTIONS DR. SUWELACK AG, Billerbeck (DE)

(*) Notice: Subject to any disclaimer, the term of this patent is extended or adjusted under 35 U.S.C. 154(b) by 127 days.

(21) Appl. No.: 14/131,688

(22) PCT Filed: Jul. 11, 2012

(86) PCT No.: PCT/EP2012/063522
§ 371 (c)(1),
(2), (4) Date: Feb. 17, 2014

(87) PCT Pub. No.: WO2013/007732
PCT Pub. Date: Jan. 17, 2013

(65) Prior Publication Data
US 2014/0163447 A1   Jun. 12, 2014

(30) Foreign Application Priority Data
Jul. 12, 2011  (EP) .................................. 11173663

(51) Int. Cl.
*A61F 13/00* (2006.01)
*A61L 15/42* (2006.01)
(Continued)

(52) U.S. Cl.
CPC .. *A61F 13/00042* (2013.01); *A61F 13/00063* (2013.01); *A61F 13/00068* (2013.01);
(Continued)

(58) Field of Classification Search
CPC ............... A61L 15/425; A61L 26/0085; A61L 26/0095; A61L 24/0036; A61L 15/44;
(Continued)

(56) References Cited

U.S. PATENT DOCUMENTS 4,541,426 A * 9/1985 Webster .................. A61L 15/58
602/47
5,254,133 A * 10/1993 Seid .................... A61B 17/0057
128/899
(Continued)

FOREIGN PATENT DOCUMENTS

WO       01/89431 A1    11/2001
WO    WO 0189431 A1 *  11/2001  ............. A61F 13/02
(Continued)

OTHER PUBLICATIONS

International Search Report for corresponding PCT/EP2012/063522 dated Aug. 6, 2012, two pages.
International Preliminary Report On Patentability for corresponding PCT/EP2012/063522 dated Jan. 23, 2014, seven pages.

*Primary Examiner* — Rachael E Bredefeld
*Assistant Examiner* — Caitlin A Carreiro
(74) *Attorney, Agent, or Firm* — Medler Ferro Woodhouse & Mills PLLC

(57) ABSTRACT

Wound treatment materials can have at least two perforated biomatrix layers which are interconnected. Methods for preparing such wound treatment materials include the application of adhesives. Treatment of exuding wounds, and vacuum-assisted wound treatment therapy, can be carried out with the wound treatment materials.

15 Claims, 10 Drawing Sheets

(51) Int. Cl.
  *A61L 15/28* (2006.01)
  *A61L 15/32* (2006.01)
  *A61L 15/22* (2006.01)
  *A61F 13/02* (2006.01)

(52) U.S. Cl.
  CPC .... *A61F 13/00995* (2013.01); *A61F 13/0213* (2013.01); *A61F 13/0226* (2013.01); *A61F 13/0246* (2013.01); *A61F 13/0253* (2013.01); *A61L 15/225* (2013.01); *A61L 15/28* (2013.01); *A61L 15/325* (2013.01); *A61L 15/425* (2013.01)

(58) Field of Classification Search
  CPC .......... A61L 15/64; A61L 15/00; A61L 26/00; A61L 26/0066; A61L 26/009; A61M 27/00; A61F 2013/00863; A61F 2013/00255; A61F 2013/00251; A61F 2013/00604
  USPC ................ 602/41–19, 41–49, 50–52, 58, 59; 604/358–402, 304; 424/443–447; 128/888
  See application file for complete search history.

(56) References Cited

U.S. PATENT DOCUMENTS

| | | | | |
|---|---|---|---|---|
| 5,362,761 | A | * | 11/1994 | Uragami .............. B01D 67/003 521/154 |
| 5,635,201 | A | * | 6/1997 | Fabo ................... A61F 13/0276 424/443 |
| 6,179,872 | B1 | * | 1/2001 | Bell ....................... A61L 27/24 428/304.4 |
| 7,074,981 | B2 | * | 7/2006 | Chalmers .......... A61F 13/00017 602/41 |
| 2006/0029650 | A1 | | 2/2006 | Coffey |
| 2007/0225663 | A1 | | 9/2007 | Watt et al. |
| 2009/0149823 | A1 | | 6/2009 | Orgill et al. |
| 2010/0100022 | A1 | * | 4/2010 | Greener ............ A61F 13/00021 602/44 |
| 2010/0106117 | A1 | * | 4/2010 | Lockwood .......... A61M 1/0058 604/319 |

FOREIGN PATENT DOCUMENTS

| | | | | |
|---|---|---|---|---|
| WO | WO-0189431 A1 | * | 11/2001 | .......... A61F 13/022 |
| WO | 2005/123170 A1 | | 12/2005 | |
| WO | 2009/012438 A2 | | 1/2009 | |

\* cited by examiner

PERFORATED, LAYERED WOUND TREATMENT MATERIAL

The present invention relates to wound treatment materials comprising at least two perforated biomatrix layers which are interconnected by means of a connecting agent, as well as to methods for producing such wound treatment materials, and to the use thereof, particularly in the treatment of exuding wounds, and in vacuum-assisted wound treatment therapy.

INTRODUCTION AND BACKGROUND OF THE INVENTION

In the field of wound care and wound treatment, the application of mechanical and electrical treatment methods has been established in addition to the use of conventional wound dressings. In particular, the negative pressure or vacuum process has been established in order to achieve a more rapid wound healing. This method is known in the medical field by the term Negative Pressure Wound Therapy (NPWT) or vacuum therapy.

In this form of therapy an almost deep wound is equipped with a synthetic or semi-synthetic filling, sponge or foam material, such as a cotton gauze or a polyurethane (PU), polyethylene (PE) or polyvinyl alcohol (PVA) sponge and taped airtight with a thin polymer film. In this wound area a negative pressure, which is usually at 80-140 mm below the external pressure, is then applied via a flexible tube by means of an external pump. This effects a pulling together of the wound edges and draining of the wound fluid. Furthermore, "micro-massage effects" (also known as "microstrain" effect) may enable cell growth and stimulation of new tissue formation.

Due to the healing successes that can be achieved with this method, this method is successfully applied worldwide.

In the course of wound healing fresh, healthy tissue is formed by new cell growth. Improved tissue regeneration is particularly observed in the application of a vacuum assisted wound treatment. In this case, however, tissue cells tend to grow into the used filling or sponge materials.

Accordingly, in particular the following disadvantages have been found with the conventional use:

When using synthetic filling, sponge or foam materials, especially when using common polyurethane foams and other conventional synthetic and semi-synthetic wound dressings, an ingrowth of the newly formed tissue into the filling material or sponge or foam occurs. As a result, the filling material cannot easily be removed from the wound during dressing changes or after completion of the therapy, but often has to be removed surgically. This can damage the newly formed healing tissue, in the worst case, the newly formed tissue is removed again by the surgery, both of which being generally detrimental to the progress of wound healing. Moreover, such an additional surgical procedure represents a significant effort, which is connected with unnecessary pain for the patient and a treatment delay.

In addition, the tissue newly formed under a conventional vacuum therapy often does not exhibit a high rigidity, is cosmetically inferior and therefore the healed site tends to reopen and needs to be treated gently. This represents a significant impairment of quality of life of the patients.

Particularly to overcome the problem of ingrowth into the filling material, numerous approaches exist, wherein in the vacuum therapy so-called biodegradable or bioresorbable materials such as biomatrix materials or materials of natural origin are used on the side facing towards the wound.

Accordingly, wound treatment materials based on biomatrix materials for treating chronic and exuding wounds and in particular for use in the vacuum-assisted wound therapy treatment are in principle already known.

For example, WO 2007/016664 describes a method for treating wounds using vacuum therapy, wherein a granular or particulate collagen material or a dispersed collagen mass is introduced into the wound, covered with conventional wound dressing materials and connected to a vacuum drainage system to achieve a better compatibility of the vacuum therapy. Although collagen in granular or particulate form or as a dispersed mass can easily be sprinkled or incorporated into deep wounds or skin defects, its use is however disadvantageous in that its positioning in the wound can hardly or not at all be corrected once it came in contact with the wound fluid as it usually immediately glues or adheres to the wound bed. A uniform, planar application is especially difficult when using granular or particulate material and usually strongly depends on the skill and experience of the practitioner.

Similar problems occur when using materials in the form of dispersed masses, which can be well molded to the wound surfaces, whereas homogeneous application to the wound area is limited. In addition, such water-based formulations always bear the problem of stabilization and preservation against microbial attacks. On the one hand this requires specific additional efforts when manufacturing such products and on the other hand bears the risk of unwanted side effects or intolerance reactions during the application, in particular when using chemical preservatives.

Other approaches include the use of layered biomaterials, in particular those in the form of a sheet, fleece, pad, layer, or in the form of a mask or a compress, which can be applied to at least one portion of the human or animal body and which can remain in the body or can be physiologically implemented or degraded due to their bioresorbability or which are removed as part of treatment.

Wound treatment materials with such a layered biomatrix based on collagen and their use in the vacuum therapy are, for example, the subject of US 2003/0078532 and US 2007/0027414. However, both publications solely relate to materials, comprising a single bioresorbable collagen layer in connection with a bioinert synthetic filler or coating layer, such as a synthetic sponge material. The bioinert synthetic materials may have perforations. A perforated biomatrix layer or a material having a plurality of connected biomatrix layers is not mentioned therein.

The US 2002/115952 describes a wound treatment material for vacuum therapy, comprising on the side facing towards the wound a bioabsorbable polymer matrix, such as collagen, which is connected with a synthetic open-cell polyurethane or polyethylene foam. Therein the possibility is mentioned to remove the synthetic foam material and to leave the bioabsorbable layer in the wound during a dressing change. Herein, no material having a plurality of connected biomatrix layers is mentioned either. Furthermore, no perforation of the bioabsorbable layer is described.

Furthermore, for example. WO 2009/012438, relates to a vacuum wound treatment material in the form of a porous scaffold material, which is coated with a hemostatic agent such as collagen. Such coating is present in a range of 0.01-100 microns.

Object of the WO 2005/123170 are further vacuum wound treatment materials based on biodegradable scaffold materials, in particular of mixtures of collagen and oxidized regenerated cellulose, which may be present in combination with non-resorbable materials.

Both of the aforementioned documents do not describe materials having a plurality of interconnected perforated biomatrix layers.

US 2007/0185426 relates to vacuum wound treatment materials, too, wherein in particular 3-layer materials comprising a bioabsorbable collagen layer facing the side towards the wound, a middle layer of a hydrogel-forming or water-soluble polymer such as of gelatin, collagen, alginate or chitosan, and a final layer of a synthetic open-cell polyurethane or polyethylene foam. The water-soluble hydrogel layer allows on the one hand to resolve the synthetic foam from the bioresorbable collagen layer, and on the other hand this hydrogel layer acts as a barrier layer, which prevents ingrowth of cells in the overlying PU foam. Then, however, wound healing and cell growth is selectively stopped by reaching the barrier layer. Accordingly, no materials are described either, which exhibit a plurality of biomatrix layers connected with each other for example via such hydrogel layers and which further enable layer-wise cell seeding of the individual layers. No perforation of the collagen layer is mentioned either.

A further vacuum wound treatment material having a biomatrix layer, in particular a collagen layer, is the subject of US 2001/0043943 and the corresponding US 2003/0208149 and WO 2001/089431. The collagen material used therein is purified, acellularised small intestine submucosa tissue ("small intestine submucosa"; SIS) and thus purified intact tissue material that can also be provided with perforations. Here, the collagen material is introduced into the wound together with a further cover or filling layer. Although, it is mentioned that also a plurality of SIS layer materials may be used, however nowhere it is mentioned to interconnect them by connecting means, in particular a water-soluble bonding agent. In addition, herein, no porous scaffold-like collagen materials are mentioned to form the interconnected perforated biomatrix layers, but only intact tissue material (SIS).

OBJECT OF THE INVENTION

The object of the present invention was to provide a new and improved wound treatment material, in particular for use in the treatment of exuding wounds and for use in the vacuum wound treatment therapy, that has a high compatibility, optimal absorbability, good and easy applicability and adequate permeation and also allows optimal monitoring of the wound healing process.

DESCRIPTION OF THE INVENTION

The present inventors have surprisingly found that the present object has been solved by providing wound treatment materials comprising at least two perforated biomatrix layers which are interconnected by means of a connecting agent.

Wounds to be treated by means of vacuum therapy are mostly deep wounds, i.e. wounds which are deeper than 0.5 cm. The wound treatment materials used should thus also have a sufficient total layer thickness to line the wound. The usual polyurethane foams have a thickness between 1.5 and 3.0 cm and are compressed under vacuum to approximately 0.4 to 0.6 cm.

Collagen materials are usually less compressible and are very quickly seeded due to their physico-chemical structure, so here in principle thinner pads with about 0.4 to 2.0 cm total thickness would be sufficient. Due to the lower compressibility such a collagen material can, however, not be adapted to wound unevenness as good as the conventional synthetic PU or PE sponges.

When using wound treatment materials in the vacuum therapy, care must also be taken to ensure that the wound treatment materials ensure good drainage of wound exudate, namely have a sufficient permeation capacity. Stressed wounds, for example, chronic wounds, generate a large amount of wound fluid, which may interfere with wound healing, since an excessive exudation can lead to edema and maceration. Such wounds are also called exudative or highly exuding wounds. By applying vacuum, it is possible to drain the wound fluid (exudate) and to transmit the negative pressure to the wound bed via the wound dressing.

Laboratory experiments on a simulated wound surface showed that the use of conventional collagen materials in the form of a layer results in a quick drop of the negative pressure and in a poor drainage of exudate, because the collagen interacted with the exudate and got choked and was thus so far reduced in his permeation capacity that no effective vacuum could be established.

If in view thereof only a thin collagen layer is used in combination with the conventional vacuum suitable synthetic foam materials, as known from the prior art, the risk occurs, especially with long-lasting dressing change intervals or with quickly granulating wounds, that the individual thin collagen layers are quickly completely seeded and that subsequently also the overlying synthetic foam layer is seeded with cells, which in turn can result in the need for surgical removal.

It should in particular also be noted that the individual wound healing rates can be different. Therefore, an estimation how fast the wound bed heals or penetrates the bioresorbable matrix layer or whether ingrowth into the overlying synthetic filling layers has already occurred is limited and based on a case by case evaluation. Thus it is difficult for the practitioner, when changing the dressing, to estimate the wound healing progress, because the healing wound is so to say located amongst the wound treatment material. To determine the healing progress, opening the wound by force or by cutting would be necessary.

In an extreme case it is conceivable that the wound accrues very quickly so that the dressing has already been seeded completely before a dressing change has taken place. In such a case, the risk occurs that the wound bed grows into or adheres to the synthetic filler cover layer, usually a synthetic filler or foam material, which can lead to difficulties when changing dressings or in the healing process as explained before.

Against this background, the present inventors have surprisingly found that a wound treatment material formed of several biomatrix layers joined to each other, represents a particularly useful alternative to the known layered materials in the form of a biomatrix layer on a synthetic filler.

By suitable choice of the number of biomatrix layers and by varying the thicknesses of the individual biomatrix layers the total layer thickness of the wound treatment material can be arbitrarily varied and perfectly adapted to the necessary treatment conditions.

By using a layered material, the practitioner is also able to ablate or remove the material layer by layer during the dressing change and, for example, first remove only as many layers of the dressing until he arrives at layers grown with tissue, the so called wound base. As already mentioned, due to the different wound healing rates one or more layers facing towards the wound can be seeded. The upper, not yet seeded layers of the wound dressing can thus easily be removed without causing a trauma to the wound bed.

Particularly advantageous connecting means have been found to be soluble or separable in an aqueous environment, especially under physiological wound conditions or in wound exudate, and which are sufficiently separated when the wound treatment material is soaked with the exudate, so that the individual biomatrix layers easily detach and can be separated from each other, in particular without the use of mechanical aids, surgical intervention or a high expenditure of force.

To avoid these problems of decreasing permeation capacity and liquid permeability with increasing wound treatment material thickness, it is important that the interconnected biomatrix layers have perforations and that these perforated biomatrix layers are connected to each other in a way that continuous perforations, openings or channels are present throughout the total thickness of the wound treatment material, or that upon dissolution of the connecting means such continuous perforations, openings or channels are formed, so that the permeation or the fluid drainage throughout the entire thickness of the composite material during the entire treatment is ensured.

When used in exuding wounds the wound dressing is usually completely wetted within a few hours, and the material should in principle be suitable for use over several days, preferably about 2 to 7 days. In principle an application period up to 14 days is possible.

Particularly when using connecting means which are soluble in physiological wound milieu, it becomes apparent that with the dissolution or the reduction of the adhesion or the separation of the connection of the individual biomatrix layers they become able to slide easily over adjacent layers, they almost "swim" on each other in the wound environment. Therewith, the holes, slots or openings of the individual perforated biomatrix layers, which were originally positioned directly above the other in the tightly connected condition, may move among each other in a way, that openings of individual layers are completely covered by overlying or underlying layers and thus interrupt the continuous perforations throughout the total thickness of the wound treatment material, which deteriorates the drainage and reduces the permeation capacity. In extreme cases, the layers can move as far as that the drainage is completely blocked.

To avoid this detrimental and unwanted blockade of the continuous perforations, the individual perforated biomatrix layers are preferably arranged such that the holes, slots or openings of the perforations of the individual layers still form a continuous channel when the individual layers move among each other, so that at any time drainage of the wound exudate is ensured. This can be achieved by applying appropriate perforation patterns as well as by a suitable combination and variation of the perforation patterns of the individual layers. For example, this can be achieved by insertion of additional holes or slots in each of the second layer or by the skilled arrangement of slots, for example the cross-shaped arrangement of two layers on each other.

Surprisingly, the wound treatment materials thus obtained also have a higher flexibility and thus a better conformability to the wound compared to one-piece (non-layered) biomatrix materials with similar total thickness.

Another advantage of the perforations can be seen in the possibility to more easily detach layers which grew together with the wound sides, due to the holes or slots, as the holey structure provides a kind of perforation, along which layer residues which have not been grown can be separated by cutting or tearing, so that the edge parts of an ingrown biomatrix layer may remain in the wound, while the central or main part of such layer is removed.

The wound treatment material of the present invention is mainly formed of two or more biomatrix layers which are suitable for the use as a skin or wound dressing according to the invention, or, if applicable, for application of active ingredients and care substances, and in particular for the absorption of liquids such as wound exudate or blood.

In the sense of the present invention, a biomatrix layer is understood to be a layer-shaped biomatrix or a dressing in the form of a layer, a sheet, a fleece, a pad, sponge or foam or in the form of a mask or compress, having a substantially planar configuration, which is formed from a biocompatible substantially completely or partially bioresorbable or bioabsorbable carrier material.

The carrier materials of biomatrix layers according to the present invention exhibit good biocompatibility, are thus physiologically acceptable to skin and mucus membranes and have no toxicological potential and do not provoke irritation effects or other intolerance reactions, neither when applied to intact skin nor when applied to wounds, and are pharmacologically safe.

The wound treatment materials according to the invention are composed of at least two such layer-shaped biomatrix layers in the manner of a so-called "sandwich-layer". According to the invention a biomatrix layer particularly relates to those with a layer thickness (shortest side length) of 10 mm at a maximum.

Known and common layer-shaped biomatrices in the form of planar configurations such as in the form of sheets, fleeces, compresses, pads etc. comprise, for example, planar or layer-shaped continuous wound dressings based on collagen in the field of treatment of chronic wounds, or hemostatic agents, such as those as known under the tradename Matriderm®, Matristypt® or Puracol® from the company Dr. Suwelack Skin & Health Care AG or Suprasorb C® from the company Lohmann & Rauscher, Promogran® from the company Johnson & Johnson or Systagenics or Avitene® sheets of Davol Inc. Further wound treatment agents, which are also used in vacuum therapy, are, for example, commercially available under the tradename Integra® single layer or Integra® bilayer from the company Integra®. Furthermore, well-known examples of planar, layer-shaped wound dressings based on polysaccharides include Algisite M® from Smith & Nephew, Askina Sorb® from B. Braun and many more. Also planar, sheet-like wound dressings based on other polysaccharides such as Chitoskin® from Sangui BioTech GmbH or mixtures of e.g. collagen and alginate such as Fibracol® from Johnson & Johnson are known and used as common wound treatment agents, both in the treatment of chronic wounds and as hemostatic or hemostatic agent.

In principle, such prior art wound dressings on the basis of biomatrix materials may be used in the wound treatment materials according to the present invention to form the perforated biomatrix layers, too.

Particularly preferred are planar or layer-shaped biomatrix materials, which are characterized by a good and uniform large-scale applicability and a good modeling and positioning on the treated skin area, which in particular can be achieved by using biomatrix layers with high flexibility for a spatial or three-dimensional modeling. In particular in the treatment of wounds with deep skin defects or large wound cavities then the most complete and homogeneous filling or lining or tamponade of such deep skin defects or wound cavities can be achieved with the flexible biomatrix layer material.

Furthermore, the carrier material must be selected to exhibit sufficient stability in order to be converted, for example by cutting and perforating, into the perforated biomatrix layers of the present invention. In addition, the biomatrix layers of the present invention should have sufficient mechanical stability in order to remain dimensionally stable and not to tear during use or during the course of the application, neither in the dry nor in the moist state.

The carrier material, which substantially forms the biomatrix layers, is preferentially chosen from the group of the natural hydrophilic materials, i.e. materials that are capable of being wetted with water. It is preferably a so-called structure-former or a structure-forming polymer, especially from the group of animal or plant derived hydrocolloids, accordingly a partly water-soluble or water-swellable natural, structure-forming polymer. Particularly preferred are structure-forming hydrocolloids from the group of the proteins, of the polysaccharides and/or of the glucosaminoglycanes.

Particularly preferably the carrier material of the biomatrix layers is selected from the group of the proteins, such as, for example, from the group of collagens, for example soluble or insoluble, fibrillar, animal or plant collagen, or gelatine, elastin (comprising elastin hydrolysate), keratin, fibroin, albumins, globulins such as lactoglobulin, milk proteins such as casein. In this connection collagen is quite particularly preferred, optionally also in a mixture with further fibrillar proteins or in a mixture with gelatine or particularly preferably in a mixture with elastin.

In the case of carrier materials on the basis of collagen it is preferably a question of those which are processed and produced by processes known from the state of the art and, for example, from DE 40 28 622 or from DE 103 50 654. The collagen carrier materials that are preferred in accordance with the invention are, in particular, characterized by outstanding hydration properties and by a good liquid-uptake capacity or absorbency, an aspect which is advantageous in particular with a view to taking up large amounts of liquid, for example in the case of heavily exuding or bleeding wounds, and also by the anti-irritant and wound healing properties thereof. By reason of the structural similarity to human skin and human tissue, types of collagen are preferably selected that occur in skin and tissue, in particular collagen of types I, III and V. As a result, the particularly good compatibility and biocompatibility as well as the good biodegradability of the biomatrix layers on the basis of such collagen carrier materials, is determined, as the same are biologically degradable and can be metabolised in natural manner when they remain in the body or during the process of wound healing.

The collagen carrier material that is used in accordance with the invention is preferably obtained from sources of collagen of bovine, equine and porcine origin. The collagen can be obtained from the conventional sources such as hides or tendons by conventional processes.

Furthermore, use may also be made of collagen materials that have been subjected to a crosslinking reaction. In this case a thermal crosslinking, so-called dehydrothermal crosslinking, is preferred. Furthermore, crosslinking with chemical crosslinkers is possible. These include, in particular, aldehydes such as glutaraldehyde; carbodiimides such as EDC; isocyanates; epoxides or imidazoles, with the epoxide from the group of the chemical crosslinkers being particularly preferred.

Likewise preferred carrier materials that are selected from the group of the polysaccharides include, for example, homoglycanes or heteroglycanes, such as, for example, alginates, especially sodium alginate or calcium alginate or mixtures thereof, carrageen, pectins, tragacanth, guar gum, carob-bean flour, agar-agar, gum arabic, xanthan, natural and modified starches, dextranes, dextrin, maltodextrins, chitosan, glucanes such as β-1,3-glucane or β-1,4-glucane, cellulose, oxidized regenerated cellulose (ORC) etc. Particularly preferred polysaccharides are alginates, in particular sodium alginates and calcium alginates and oxidized regenerated cellulose or mixtures thereof.

The group of the carrier materials that are selected from the group of the polysaccharides likewise includes such materials that have been subjected to a crosslinking. In particular, crosslinked polysaccharides include alginates crosslinked with calcium ions.

Glucosaminoglycanes (GAGs/mucopolysaccharides) include, for example, hyaluronic acid, chondroitin sulfate, dermatan sulfate, keratan sulfate, heparan sulfate, heparin etc. Hyaluronic acid is particularly preferred.

Furthermore, use may also be made of biomatrix layers based on carrier materials that have been selected from the group of the bioabsorbable synthetic or modified natural polymers, including, for example, polylactides or polylactic acids (PLA), polyglycolic acid (PGA), polycaprolactones (PCL), polydioxanones (PDO), polylactide coglycolides (PLGA), polytrimethylene carbonate etc.

Use may also be made of biomatrix layers, which comprise mixtures of at least two different carrier materials from the aforementioned carrier materials. In this connection, in particular biomatrix layers based on mixtures of collagen with gelatine, elastin, alginates, gludosaminoglycanes such as hyaluronic acid (GAGs), PLA or PGA, as well as based on mixtures of alginates with collagen, gelatine, elastin, glucosaminoglycanes such as hyaluronic acid, PLA or PGA are preferred.

As a matter of principle, the carrier materials of the biomatrix layers according to the invention may also contain small amounts of synthetic and/or semi-synthetic and/or modified natural polymers, such as, for example, those which have been selected from the group comprising, for example, cellulose ethers, polyvinyl alcohol, polyvinyl pyrrolidone, synthetic cellulose derivatives such as methylcellulose, carboxycellulose, carboxymethylcellulose such as, for example, sodium carboxymethylcellulose, cellulose esters, cellulose ethers such as hydroxypropylcellulose, cationised celluloses or cationised starches etc., polyacrylic acid, polymethacrylic acid, poly(methylmethacrylate) (PMMA), polymethacrylate (PMA), polyethylene glycols, polyurethanes, polyurea compounds etc. and mixtures thereof. A preferred synthetic polymer is polyacrylate or polyacrylic acid, which quite particularly preferably, for example, may be contained in the biomatrix layers in a mixture with carrier materials that have been selected from the alginates. Preferred semi-synthetic or modified natural polymers are those including cellulose, carboxymethylcellulose, cationised celluloses or cationised starches.

In this connection the amount of such synthetic and/or semi-synthetic and/or modified natural polymers in the biomatrix layers according to the invention lies, as a rule, below 40 wt. %, more preferably below 25 wt. %, still more preferably below 10 wt. %, in each instance relative to the total weight of the dry biomatrix layers.

Quite particularly preferred, however, are those biomatrix layers which contain no synthetic carrier materials, in which connection the bioabsorbable synthetic or modified natural polymeric carrier materials described above are not meant here.

The amount of the aforementioned bioabsorbable synthetic or modified natural polymers in the biomatrix layers according to the invention lies, as a rule, below 70 wt. %, more preferably below 60 wt. %, still more preferably below 50 wt. %, in each instance relative to the total weight of the dry biomatrix layers.

In accordance with the invention biomatrix layers based on crosslinked carrier materials are suitable, too, since crosslinked materials exhibit a particularly high mechanical stability. As a result, biomatrix layers comprising crosslinked carrier materials are particularly well suited in order to apply the perforations according to the invention. Particularly preferred are biomatrix layers based on crosslinked collagens, especially based on dehydrothermally or epoxide-crosslinked collagens such as described, for example, in the non-published EP-application 10196934.3 of the present applicant, as well as alginate materials crosslinked with calcium ions.

In order to achieve an optimal granulation or wound healing, it is also important to select biomatrix materials which support the growth of the body's own cells and thus the formation of intact tissue structures, which is particularly given by having a scaffold or a so-called "scaffold" function. Surprisingly, it has been found that in particular freeze-dried, porous biomatrix materials exhibit, despite their relatively fine porosity of its sponge-like structure, a high biocompatibility and can be well seeded. From the prior art fine-porous synthetic materials are known, too, which usually do not allow seeding. The particular suitability of the fine-pored freeze-dried collagen materials, besides the "scaffold" function, can in particular also be ascribed to their structural similarity with the skin and tissue, as well as to the high degree of homogeneity due to the manufacturing process.

Biomatrix layers of the present invention are preferably obtainable by a process comprising the steps of:
a) preparing an aqueous suspension or a solution of at least one structure-forming natural polymer;
b) optionally mixing one or more active and/or auxiliary substances;
c) pouring the mixture into a suitable mold;
d) drying, preferably freeze-drying, of the mixture to obtain a porous molded body;
e) optionally cutting the molded bodies obtainable from step d) in layers;
f) optionally, cutting of the layers from step e) into the desired geometric shape of the biomatrix layers and
g) optionally perforating the biomatrix layers.

Preferably, in step c) large-size sheets or blocks with a relatively large thickness (approximately 1 to 10 cm) are poured, which are then cut in step e) into the desired layer thickness of 0.5 to 10 mm. However, it is also possible to pour the material in step c) directly into the desired layer thickness followed by drying.

Suitable methods for obtaining such porous freeze-dried biomatrices are described, for example, in DE 4028622, DE 10350654, WO 04/104076, WO 05/113656 or WO 08/020,066 of the present applicant and the disclosure thereof being entirely encompassed herein.

In accordance with the foregoing explanations, the individual biomatrix layers can either be formed entirely from a suitable carrier material or consist a major part thereof. For example, the biomatrix layers may be based on a carrier material with additional active substances and/or auxiliary agents being added.

Active substances include, in particular, cosmetic or therapeutic or pharmaceutical active substances that are suitable for external use.

Examples of cosmetically active compounds, optionally also, for example, of dermatological, therapeutically active compounds include: antimicrobial agent such as antiseptic active substances and antibiotics, astringent agents, conditioning agents for the skin, skin-smoothing agents, agents for intensifying the hydration of the skin such as, for example, glycerine or urea, keratolytics, radical-interceptors for free radicals, active substances that modulate the differentiation and/or proliferation and/or pigmentation of the skin, vitamins and provitamins such as, for example, beta carotene, vitamin A, B, E etc., vitamin C (ascorbic acid) and their derivatives, such as, for example, glycosides such as ascorbyl glucoside, or esters of ascorbic acid, such as sodium or magnesium ascorbyl phosphate or ascorbyl palmitate and stearate. L-ascorbic acid phosphate esters, alkali-metal salts such as sodium salts and potassium salts of L-ascorbic acid phosphate esters; alkaline-earth-metal salts such as magnesium salts and calcium salts of L-ascorbic acid phosphate esters; trivalent metal salts such as aluminium salts of L-ascorbic acid phosphate esters; alkali-metal salts of L-ascorbic acid sulfate esters such as sodium salts and potassium salts of L-ascorbic acid sulfate esters; alkaline-earth-metal salts such as magnesium salts and calcium salts of L-ascorbic acid sulfate esters; trivalent metal salts such as aluminium salts of L-ascorbic acid sulfate esters; alkali-metal salts such as sodium salts and potassium salts of L-ascorbic acid esters; alkaline-earth-metal salts such as magnesium salts and calcium salts of L-ascorbic acid esters; and trivalent metal salts such as aluminium salts of L-ascorbic acid esters.

Active substances with irritant side-effect, such as alpha-hydroxy acids, β-hydroxy acids, alpha-keto acids, β-keto acids, retinoids (retinol, retinal, retinoic acid), anthralins (dioxyanthranol), anthranoids, peroxides (in particular, benzoyl peroxide), minoxidil, lithium salts, antimetabolites, vitamin D and its derivatives; catechols, flavonoids, ceramides, polyunsaturated fatty acids, essential fatty acids (e.g. gamma-linolenic acid), enzymes, coenzymes, enzyme inhibitors, hydrating agents, skin-soothing agents, detergents or foam-forming agents, and inorganic or synthetic matting fillers, or decorative substances such as pigments or dyestuffs and particles.

Furthermore, extracts of plant active substances and extracts or individual substances obtained therefrom may be mentioned. Generally, the extract of plant active substance is, as a rule, selected from the group consisting of solid plant extracts, liquid plant extracts, hydrophilic plant extracts, lipophilic plant extracts, individual plant components; as well as mixtures thereof, such as flavonoids and their aglycones: rutin, quercetin, diosmin, hyperoside, (neo)hesperidin, hesperitin, Ginkgo biloba (e.g. ginko flavone glycosides). *Crataegus* extract (e.g. oligomeric procyanidins), buckwheat (e.g. rutin), *Sophora japonica* (e.g. rutin), birch leaves (e.g. quercetin glycosides, hyperoside and rutin), elder blossom (e.g. rutin), lime blossom (e.g. essential oil with quercetin and farnesol), St. John's wort oil, olive-oil extract, calendula, arnica (e.g. oily extracts of the blossoms with essential oil, polar extracts with flavonoids), melissa (e.g. flavones, essential oil); immunostimulants: Echinacea purpurea (e.g. alcoholic extracts, fresh vegetable juice, pressed juice). Eleutherokokkus senticosus; alkaloids: caffeine, theine, theobromine, rauwolfia (e.g. prajmaline), evergreen (e.g. vincamine); further botanicals: aloe, horse chestnut (e.g. aescine), garlic (e.g. garlic oil), pineapple (e.g. bromelains), ginseng (e.g. ginsenosides), milk-thistle fruits (e.g. extract standardised to silymarin), mouse-thorn root (e.g. ruscogenine), valerian (e.g. valepotriates, valerian tincture), kava kava (e.g. kavalactones), hop flowers (e.g. hop bitters), passifloraceous extract, gentian (e.g. ethanol extract), anthraquinone-containing drug extracts, for example, aloin-containing aloe-vera juice, pollen extract, algae extracts, liquorice-root extracts, palm extract, *Galphimia* (e.g. mother tincture), mistletoe (e.g. aqueous ethanol. extract), phytosterols (e.g. beta-sitosterol), mullen flowers (e.g. aqueous alcoholic extract), *Drosera* (e.g. liqueur-wine extract), sea-buckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from *Norolaena lobata, Tagetes lucida, Teeoma siems, Momordica charantia*, aloe-vera extracts and mustard oils.

As distinct from the active substances described above which are used substantially in the cosmetic field, in the case of the therapeutic active substances (medicaments) it is a question of those which in the sense of the Arzneimittelgesetz [German Drugs Act] are, inter alia, intended to heal, alleviate or prevent diseases, afflictions, bodily defects or pathological complaints. In accordance with the invention, in particular such agents or active substances are suitable which are intended for external or transdermal use, in particular in the field of wound treatment and wound healing and also in the field of the treatment of burn injuries.

In the case of active substances for a dermal or transdermal use it is a question, in particular, of cutaneously active but also of transdermal active substances. They include, for example: agents for treating burn injuries, agents for treating skin diseases, externally applicable analgesics, for example, dextropropoxyphene, pentazocine, pethidine, buprenorphine; antirheumatics/antiphlogistics (NSAR), for example, indomethacin, diclofenac, naproxen, ketoprofen, ibuprofen, flurbiprofen, salicylic acid and salicylic-acid derivatives such as acetylsalicylic acid, oxicams; steroid hormones, for example, betamethasone, dexamethasone, methyl prednisolone, ethinyl estradiol, medroergotamine, dihydroergotoxine; gout remedies, for example, benzobromarone, allopurinol; external dermatics, antihistamines, antiseptic agents such as silver, sulfadiazin, chlorhexidine, povidone-iodine, triclosan, silver salts and colloidal silver as well as metallic silver, sucralfate, quarternary ammonium compounds etc.; antibiotics such as tetracyclin, penicillin, terramycin, erythromycin, bacitracin, neomycin, polymycin B, mupirocin, clindamycin, doxicyclin etc.; antimycotics, peptide medicinal substances, antiviral active substances, anti-inflammatory active substances, antipruritic active substances, anaesthetising active substances, for example benzocaine, corticoids, antiparasitic active substances; externally applicable hormones; venous therapeutics; immunosuppressants etc., all for dermal or transdermal use; bioactive glass and silicates with granulation promoting and antiseptic effect.

Preferred therapeutic agents for dermal and transdermal use are agents for treating skin diseases such as, in particular, those which are employed in the field of wound treatment, in particular for treating chronic wounds, decubitus ulcer, varicose ulcer, diabetic foot syndrome etc., such as, for example, analgesics, for example immunosuppressants, hormones, anaesthetising active substances, antiparasitic, fungicidal or antimycotic and antibacterial (antiseptic and antibiotic) active substances such as, in particular, silver-containing active substances such as, for example, silver nitrate, silver chloride, silver iodide, colloidal silver as well as metallic silver or further silver-containing wound-treatment substances known from the state of the art, active substances for supporting and regulating the wound milieu, such as, in particular, electrolytes, silica, mineral substances and trace elements such as, for example, potassium, magnesium, calcium, selenium, iodine etc., bioactive glasses and silicates with granulation promoting and antiseptic effect, active substances for achieving a debridement of the wound, such as, for example, collagenases or other suitable proteolytic enzymes and also active substances for assisting wound healing that are known in the state of the art, such as, for example, growth factors, enzyme inhibitors, platelet rich plasma, thrombocytes, as well as extracellular matrix compounds and soluble (low molecular) protein and peptide components, preferably such as selected from the group comprising elastin, elastin hydrolysate, glycosaminoglycane, such as heparan sulphate, chondroitin sulphate, dermatan sulfate, keratin sulfate, heparin and hyaluronic acid, proteoglycans such as aggrecan, fibromodulin, decorin, biglycan, versican, perlecan, basement membrane proteoglycan with high density, syndecan and serglycin, fibrin, fibronectin, glucans such as paramylon etc.

Further preferred active substances are those which exhibit a styptic or haemostatic action, such as, for example, thrombin, fibrinogen or cholesteryl sulfate (e.g. sodium cholesteryl sulfate) or active substances with activating action on factors and substances of the extrinsic and/or intrinsic coagulation cascade, such as, for example, phospholipids, kaolin, aprotinin, factor or factor concentrates, tissue factor or calcium ions.

The carrier materials of the biomatrix layers, in particular those on the basis of proteinogenic polymers such as, in particular, collagen or plant polymers such as polysaccharides, may also have certain therapeutic effects. Accordingly, the collagen which is preferably used acts haemostatically and displays a positive, assisting effect in wound healing. The hydrocolloid (sodium) alginate which is preferably used is also said to have a certain haemostatic action. Furthermore, to a certain extent it acts antivirally. Hyaluronic acid is said to have a certain action in re-epithelialisation and as antioxidant and moisture-donor in skin care. They are, however, not active substances in the sense of the invention.

Accordingly, the perforated biomatrix layers of the wound treatment materials according to the invention may further include at least one active substance, wherein at least one active substance of the group of haemostatic agents and/or of the group of wound treatment agents is preferred.

The biomatrix layers according to the invention may further include at least one auxiliary substance.

Auxiliary substances include: pH-setting agents, such as buffer substances, inorganic and organic acids or bases; fatty substances, such as mineral oils, such as paraffin oils or vaseline oils, silicone oils, plant oils such as coconut oil, sweet-almond oil, apricot oil, maize oil, jojoba oil, olive oil, avocado oil, sesame oil, palm oil, eucalyptus oil, rosemary oil, lavender oil, pine oil, thyme oil, mint oil, cardamom oil, orange-blossom oil, soya oil, bran oil, rice oil, rapeseed oil and castor oil, wheat-germ oil and vitamin E isolated therefrom, evening-primrose oil, plant lecithins (e.g. soya lecithin), sphingolipids/ceramides isolated from plants, animal oils or fats, such as tallow, lanolin, butter oil, neutral oil, squalane, fatty acid esters, esters of fatty alcohols, such as triglycerides, and waxes with a melting-point corresponding to the temperature of the skin (animal waxes such as bees wax, carnauba wax and candelilla wax, mineral waxes such as microcrystalline waxes, and synthetic waxes such as polyethylene waxes or silicone waxes), and also all the oils suitable for cosmetic purposes (so-called cosmetic oils), as mentioned, for example, in the CTFA treatise entitled Cosmetic Ingredient Handbook, 1. Edn., 1988, The Cosmetic, Toiletry and Fragrance Association, Inc., Washington, surface-active agents in addition to the aforementioned surfactants, such as dispersing agents, wetting agents, emulsifiers etc.; fillers; stabilisers; cosolvents; pharmaceutically and cosmetically customary or other dyestuffs and pigments, in particular those which are primarily employed for the purpose of colouring the biomatrix layers and not for the purpose of application and colouring on the human body; preservatives; plasticisers; lubricants or release agents; etc.

Auxiliary substances that are preferred in accordance with the invention are buffer substances, pH-setting agents, humectants and wetting agents.

Generally the classification of the aforementioned substances in the category of the auxiliary substances within the scope of the present invention does not exclude the possibility that these auxiliary substances may also display certain cosmetic and/or therapeutic actions, which applies, to a particular degree, to the stated cosmetic oils which are preferably employed.

Wound treatment materials according to the present invention comprise at least two, preferably at least three, more preferably 3 to 10 perforated biomatrix layers.

Therein, the individual biomatrix layers of the wound treatment materials of this invention may be the same or different regarding their composition and/or their geometric shape or the type and arrangement of the respectively applied perforations.

For example, all biomatrix layers connected with each other may be formed from collagen. In this case preferably essentially identical collagen matrices may be used.

Further preferred embodiments relate to wound treatment materials which comprise perforated biomatrix layers which differ in their composition. This makes it in particular possible to provide a wound treatment material with a type of dissolution or resorption gradient, by piling biomatrix layers with different dissolution or resorption characteristics in a suitable order. For example, on the side facing towards the wound easy resorbable biomatrix layers may be provided, for example such as based on only dehydrothermally crosslinked collagen materials, onto which further collagen matrix layers with increasing crosslinking degree and thus increasing degradation stability or decreasing resorbability are applied.

It is further possible to combine biomatrix layers based on different carrier materials with each other, for example by combining collagen matrix layers with further biomatrix layers based on polysaccharides or alginates. By appropriate selection of biomatrix layer materials and piling order thus wound treatment materials with variable and optimally adjusted resorbability and applicability can be provided to achieve an optimum seeding result.

According to the invention particularly preferred are biomatrix layers based on freeze-dried porous biomatrices, in particular those based on collagen matrices, such as are obtainable, for example, by the above-mentioned methods, or by the methods disclosed in the above-mentioned publications of the applicant.

According to the invention, wound care materials are particularly preferred, wherein the biomatrix layers are freeze-dried.

According to the invention, the individual biomatrix layers each have a layer thickness (defined as the shortest distance between two points, i.e. layer thickness) of up to 10 mm. Preferably the individual biomatrix layers each have a layer thickness of up to 6 mm, more preferably up to 4 mm, even more preferred up to 3 mm. Most preferred are layer thicknesses of 1, 2 and 3 mm. In addition, layer thicknesses of at least 0.5 mm are preferred, more preferred are at least 1 mm thick layers.

The individual biomatrix layers of the wound treatment materials of this invention may be the same or different with regard to their respective layer thickness. Even by combining biomatrix layers with different layer thickness, in addition to the combination of different perforation patterns, for forming the wound treatment material according to the invention the application and resorption of these materials can be specifically controlled.

The wound treatment material of the present invention which are formed from the perforated biomatrix layers preferably has a total layer thickness or total thickness of at least 2 mm, more preferably at least 4 mm.

The total thickness is in principle not capped, they may include a total thickness of up to 30 or even up to 70 mm, with total thicknesses up to 20 mm being preferred.

To form the wound treatment material according to the invention the biomatrix layers are interconnected by connecting means.

Connecting means in the sense of the present invention include, in particular, adhesives such as spray adhesives or adhesive films, threads and sutures, staples, and other common surgical settings, such as in particular flaps and loops applied to or formed in the biomatrix layers, by which two respective adjacent biomatrix layers may be interconnected or linked with each other, or other reversible quick-release fasteners, for example such as those on the type of hook and loop fasteners, wherein one layer equipped with flexible barbed hooks and a layer provided with loops are reversible attached to each other with a hook and loop closure. The connecting means according to the invention must have a particular physiological compatibility.

Preferably, adhesives, such as liquid, semi-solid or film-like adhesives, for example polyacrylate adhesives (e.g. poly(butyl methacrylate, methyl methacrylate), polymethyl acrylate, acrylate copolymer, cyanoacrylates; tissue adhesives such as fibrin glue, albumin/glutardialdehyde glue, PEG (polyethylene glycol) based glues; spray adhesives based on synthetic, semi-synthetic or natural film formers (e.g. based on nitro cellulose, hydroxypropyl cellulose, gelatin, chitosan or alginate solutions, and mixtures thereof), conventional spray adhesives or spray-on plasters etc. are used.

According to the invention it is particularly preferred that the connecting means are soluble or resorbable in water or aqueous solutions or in a physiological environment. In this context soluble or resorbable means that the adhesive properties and the binding forces of the connecting means are reduced in the presence of water or aqueous solutions or in a physiological environment as in a wound, especially in the presence of wound exudate or blood, in a degree, that the interconnected layers easily can be separated from one another without exerting undue force or without the use of mechanical aids, such as a knife, scalpel, spatula, etc.

Suitable soluble connecting means comprise in particular water-soluble or in physiological media soluble adhesives, such as physiologically compatible spray adhesives or spray-on plasters, in particular those based on gelatin solutions, chitosan solutions, or solutions of gel-forming hydrocolloids based on sodium or potassium alginate, and mixtures thereof, in particular mixtures of gelatin and chitosan, or gelatin and alginates; as well as materials which are degradable, resorbable (metabolized) in the body, such as surgical sutures, resorbable sutures or clips (so-called staples), resorbable anchors, rivets, or screws, etc., as well as flaps and loops or hook-and-loop fasteners applied to or formed in the biomatrix layers, by which two respective adjacent biomatrix layers may be connected or linked with each other, as exemplified in FIG. 7 for flaps and loops. Further, it is possible to combine different connecting means.

Such soluble connecting means are preferred as they allow easy separation of the upper layers, facing away from the wound side, in the course of wound healing, as already mentioned in detail above.

For the above illustrated reasons, the biomatrix layers forming the wound treatment materials of this invention have perforations.

A perforation in the sense of the present invention refers to a perforation of the layer-like biomatrix materials. Therein such a perforation in particular refers to a specific application of holes or slots or channels or passages passing throughout the thickness of the material, having a substantially regular adjustment, quantity, shape and size.

Such perforations may be designed in the form of slots or holes and have a substantially triangular, rectangular, polygonal, honeycomb, circular or elliptical configuration.

In this connection, in the sense of the present invention a circular or elliptical configuration also encompasses, in principle, oval geometrical shapes, and a rectangular configuration of the portions encompasses, in principle, all known geometrical rectangular shapes. In particular, rectangles with opposing parallel and equally long sides, such as parallelograms, in particular equiangular parallelograms such as rectangles or squares, as well as diamonds or rhombi or trapezoids, are encompassed by this term.

Furthermore, perforations in any other conceivable geometrical shape or also in imaginative shapes can also be formed. For instance, it is likewise conceivable to apply the perforations in visually or aesthetically appealing shapes such as, for example, in heart-shaped or star-shaped manner etc.

Preferred are round or triangular perforations, as exemplified in FIGS. 1 to 3, as well as perforations in the form of slots or rectangular configuration. The latter may in particular also be arranged offset relative to one another, thereby forming a pattern which is comparable with a brick bond in the manner of a chimney bond or heading bond. A respective embodiment is exemplified in FIG. 4a. In a further embodiment, the perforations in the form of slots or in rectangular form may be arranged on a biomatrix layer offset relative to one another by 90°, thereby forming a pattern as exemplified in FIGS. 4b and 4c. Further, an elliptical or elongated oval perforation is possible, as exemplified in FIG. 4d.

The size of the perforations is about 1 to 15 mm, preferably about 2 to 10 mm, more preferably about 2 to 8 mm. Preferred are round perforations 2 to 8 mm in diameter, as well as triangular perforations of 4 to 10 mm side length of the triangular perforation. Further preferred are rectangular perforations with side length 0.5 to 3 mm×4 to 10 mm, preferably 1 to 2 mm×8 to 10 mm which are particularly arranged in the pattern of a brick bond or arranged offset relative to one another by 90°.

Such perforation of the biomatrix layers ensures good drainage of exudate with a low drop in pressure and an improved deformability and thus applicability of the wound treatment materials.

To guarantee exudate drainage, it is important that the perforated biomatrix layers are joined to each other in a way such that continuous perforations throughout the wound treatment material are present. Therefore, in the respective embodiments also the optionally present adhesive layers exhibit corresponding perforations and continuous perforations throughout the total thickness of the wound treatment material are present.

Particularly when using soluble connecting means the perforated biomatrix layers must be connected to each other in a way that with the dissolution of the connecting means continuous perforations throughout the wound treatment material are formed. In such embodiments optionally present adhesive layers do not have the respective perforations in the dry condition of the wound treatment materials and upon contact with the wound environment or exudate the unperforated adhesive layer is as far dissolved that continuous perforations throughout the total thickness of the wound treatment material are formed quasi in-situ.

Such embodiments of the invention relate to wound treatment materials wherein the perforated biomatrix layers are connected to one another such that continuous perforations throughout the wound treatment material are present, as well as wound treatment materials wherein the perforated biomatrix layers are connected to one another such that upon dissolution of the connecting means continuous perforations are formed.

Further embodiments relate to wound treatment materials, wherein the biomatrix layers are arranged upon each other in a way that continuous perforations throughout the wound treatment material are retained even when dissolving the connecting means and shifting of the biomatrix layers among each other.

Retaining continuous perforations throughout the total thickness of the wound treatment material even when dissolving the connecting means and shifting of the individual biomatrix layers among each other is crucial to ensure optimum drainage of exudate even in these cases, because when shifting the perforated layers among each other, the holes may be shifted against each other in a way, that the continuous channels throughout the wound treatment material are closed. This can be achieved by appropriate selection of the geometry of the perforation holes or the perforation pattern as well as a suitable arrangement of the perforated biomatrix layers to each other and in particular also by a combination of biomatrix layers each with different sized perforations.

For example, biomatrices with different sized triangular or rectangular holes may be connected to each other, or biomatrix layers with rectangular, slot-shaped or elliptical-shaped perforations are arranged offset one above the other by 90°. A respective embodiment is exemplified in FIG. 6b.

For example, one layer may have four holes and an overlying layer may have, for example, five holes, so that upon shifting the fifth hole in turn gives a passage to one of the other holes in the underlying layer. A further possibility is that the perforations in the different layers have different sizes, for example, one layer may have smaller, for example, triangles or ellipses and the overlying layer larger triangles or ellipses, no that here too, upon shifting a passage remains. Respective embodiments are exemplified in FIGS. 5 and 6a.

Wound treatment materials of the present invention are in principle obtainable by providing the perforated biomatrix layers and connecting the desired number of them in the appropriate arrangement by means of one or more suitable connecting means according to the present invention to form the layered wound treatment materials, or by connecting the desired number of suitable biomatrix layers and subsequently applying the continuous perforations forming the wound treatment materials with continuous perforations.

In the method according to the invention the perforations are formed as slots or holes and have substantially circular, triangular, rectangular, honeycomb or elliptical shapes and may in principle be formed by conventional perforating methods such as cutting or punching. Cutting may, for example, be carried out using suitable knives or cutting tools such as a roller puncher or also by laser cutting. Preferably, the perforations are applied on or in the biomatrix layers by means of punching or with laser. In the same way also the flaps and loops, used as connecting means, may be formed in the biomatrix layers.

For preparing the wound treatment materials of this invention either first the desired number of unperforated biomatrix layers is connected to one another by the desired connecting means, in particular an adhesive, and then the perforations are applied on or in the thus obtained layered material to form continuous openings or channels throughout the total thickness thereof.

Alternatively, first the perforations are applied on or in the individual biomatrix layers and subsequently they are connected to one another in the desired number and by the desired connecting means.

This is particularly advantageous if flaps and loops, formed in the biomatrices, are chosen as the connecting means, by which the individual biomatrix layers are quasi liked to one another.

Therefore, the invention, in particular, comprises a process for the preparation of a preferred wound treatment material according to the present invention, comprising the steps of a1) applying an adhesive to a biomatrix layer and applying a further biomatrix layer on the adhesive coated first biomatrix layer, optionally applying further adhesive and biomatrix layers to give the desired total thickness of the wound treatment material, and perforation of the interconnected biomatrix layers;

or a2) perforation of the biomatrix layers, applying an adhesive to a perforated biomatrix layer and applying a further perforated biomatrix layer on the adhesive coated first biomatrix layer, optionally applying further adhesive and biomatrix layers to give the desired total thickness of the wound treatment material, wherein the perforated biomatrix layers be arranged to form continuous perforations throughout the total thickness of the wound treatment material upon dissolution of the adhesive, b) optionally drying the adhesive; and c) sterilizing and/or packaging.

Preference is given to variant a2).

The solidification of the adhesive is usually carried out by drying or UV-induced crosslinking reactions, or other known methods. Preferably drying of the adhesive, particularly when using solutions of gelatin or chitosan, is carried out by drying typically at room temperature (20° C.), although higher temperatures up to 80° C. can be used, too. Decisive is that no thermal damage to the biomatrices caused by the drying temperature occurs, accordingly temperature-sensitive materials must be dried at lower temperatures, whereas less-sensitive materials can also be dried at higher temperatures.

Sterilization and packaging of the wound treatment materials of this invention can be carried out by known and conventional methods.

The invention also relates to the wound treatment material obtainable by the above method.

The wound treatment material according to the present invention may further comprise one or more cover layers of synthetic or semi-synthetic wound treatment materials.

Such embodiments relate to combination materials, wherein in addition to the biomatrix material according to the present invention, conventional wound dressing materials and synthetic materials, such as PVA. PU or PE foams or gauze are used, in particular in this case in the lower area of the wound (facing towards the wound bed) the biomatrix material of the present invention is applied and filled in the upper part with the conventional synthetic or semi-synthetic materials. This is particularly advantageous when very deep wounds are treated, in order to achieve cost-effective wound care solutions.

Particularly, the present invention also relates to the wound treatment materials of the present invention for use as a hemostatic agent as well as in the treatment of acute wounds such as traumatic or surgical wounds, e.g. tumor wounds and for the treatment of chronic wounds such as decubitus ulcer, varicose ulcer, diabetic foot syndrome etc., particularly for the treatment of exuding and heavily exuding wounds, for use as an implant (to remain in the body) as well as for use in the vacuum-assisted wound treatment therapy.

Particularly preferred is the use in the treatment of chronic and exuding wounds and in the vacuum-assisted wound treatment therapy.

The layered biomatrices according to the present invention may represent pharmaceutical products or medical devices.

Usually, the application is carried out by applying the wound treatment materials of the present invention to the body part to be treated or to the wound in dry state and being moisturized and rehydrated either through the existing wound secretion or with water or an aqueous solution or physiological saline solution, which may contain one or more active substances and/or one or more auxiliary substances. However, it is also possible to moist the wound healing materials of the present invention prior to application to the treated body part.

The wound treatment materials of the present invention are particularly suitable and intended for use in the vacuum-assisted wound treatment. Vacuum therapy, also referred to as low pressure therapy, vacuum sealing, topical negative pressure therapy (TNP), "Negative Pressure Wound Therapy" (NPWT), or "Vacuum Assisted Closure Therapy" (VAC) is a known and worldwide used method for wound healing, wherein an occlusive wound closure is combined with a transport system of wound fluid (exudate). By applying a negative pressure or vacuum to the wound, the wound is reduced, the wound edges are contracted, the healing process is accelerated and disturbing wound exudate is removed from the wound. The use in vacuum therapy according to the invention is thereby basically carried out according to the well-known and established methods.

In particular in the vacuum-assisted wound treatment, the application of the wound treatment material according to the present invention is generally carried out by introducing the wound treatment material of the invention into the wound, wherein the material is optionally cut to the shape of the wound. Optionally filling with a conventional wound dressing material or a synthetic or semi-synthetic filler or cover material is carried out. Then the wound is sealed airtight with a vacuum-tight cover sheet. Such vacuum-tight cover sheets are also known and established and can also exhibit suitable devices for mounting of drainage tubes (for example, those which are commercially referred to as T.R.A.C. Pad), suitable sealing pastes and/or sealing membranes and, where appropriate directly the drainage tubes for draining the wound fluid (drainage unit) as well as for connecting the collecting container or collection systems for the drained wound fluid as well as the negative pressure generating pump, etc.

According to the invention also included are wound treatment agents comprising a wound treatment material according to the present invention, and a vacuum-tight cover sheet, if applicable combined with the device for mounting the drainage unit. Then the wound treatment material of the present invention and the vacuum-tight cover sheet, if applicable mounted with the drainage unit, can be provided as an integral composite or individually in the form of a so-called combination or kit-of-parts-assembly.

Besides the application in the field of vacuum therapy the wound treatment materials of the present invention are also advantageous for wounds healing in conventional manner, namely by applying only the dressing as such. In such conventional treatment as well as in vacuum therapy, the medical care personnel will be capable to achieve a quick overview of the progress of wound healing simply by removing individual, not integrated layers without causing trauma to the wound.

The invention is further illustrated by the following examples. The examples are merely exemplifications, and the skilled person is able to extend the specific examples to further claimed embodiments.

EXAMPLES

Example 1 Embodiments

| No. | Biomatrix | Number of layers | Thickness of the layers | Total thickness | Connecting means | Perforation |
|---|---|---|---|---|---|---|
| 1a | collagen* | 1 | 2 mm | 2 mm | — | round, Ø 3 mm, (FIG. 1; 13) |
| 1b | collagen* | 1 | 4 mm | 4 mm | — | round, Ø 2 mm |
| 1c | collagen* | 1 | 6 mm | 6 mm | — | round, Ø 2 mm |
| 1d | collagen* epoxide-crosslinked (5%) | 2 | each 1 mm | 2 mm | — | round, Ø 2 mm (FIG. 12) |
| 2 | collagen* | 1 | 2 mm | 2 mm | — | triangular, length 4 mm (FIG. 2) |
| 3 | collagen* | 1 | 2 mm | 2 mm | — | triangular, length 8 mm (FIG. 3) |
| 4a | collagen* | 1 | 2 mm | 2 mm | — | rectangular, 1 × 10 mm (FIG. 4a) |
| 4b | collagen* | 1 | 2 mm | 2 mm | — | rectangular, 0.5 × 5 mm (FIG. 4b) |
| 4c | collagen* | 1 | 2 mm | 2 mm | — | rectangular, 1 × 10 mm (FIG. 4c) |
| 5 | collagen* | 2 | each 2 mm | 4 mm | gelatine glue | triangular, 4 und 8 mm (FIG. 5) |
| 6a | collagen* | 4 | each 2 mm | 8 mm | gelatine glue | rectangular, 1 × 10 mm 90° offset (FIG. 6a; 14) |
| 6b | collagen* | 4 | each 2 mm | 8 mm | gelatine glue | round, Ø 2 mm (FIG. 15) |
| 7 | collagen-alginate-mixture* | 1 | 2 mm | 2 mm | — | round, Ø 2 mm |
| 8 | collagen-alginate-mixture* | 2 | each 2 mm | 4 mm | gelatine glue | round, Ø 2 mm |
| 9 | collagen* | 2 | each 4 mm | 8 mm | chitosan glue | round, Ø 2 mm |
| 10 | collagen* | 2 | each 4 mm | 8 mm | gelatine/chitosan glue** | round, Ø 2 mm |
| 11 | collagen* | 2 | each 4 mm | 8 mm | gelatine/alginate glue** | round, Ø 2 mm |

-continued

| No. | Biomatrix | Number of layers | Thickness of the layers | Total thickness | Connecting means | Perforation |
|---|---|---|---|---|---|---|
| 12 | collagen* | 2 | each 4 mm | 8 mm | adhesive spray*** | round, Ø 2 mm |

*porous biomatrix, obtainable by freeze-drying of a biomatrix-suspension; optionally chemically crosslinked with epoxide;
**aqueous gelatine/chitosan or gelatine/sodium alginate glue (wt.-ratio 2:1)
***Hansaplast ® spray plaster, Beiersdorf (copolymer based on methacrylate, ethyl acetate, n-pentane)

The hole-like perforations were applied with a punch and with laser.

The biomatrix layers or wound treatment materials may further comprise additional active substances and auxiliary substances or may be prepared with higher or lower total thickness by variation of the layer thickness and/or the number of biomatrix layers.

Example 2 Investigation in the Wound Simulator

1. Experimental Setup

The central component is an aluminum block (dimensions: 150×140×60 mm) with a 2 cm deep circular milled slot with a diameter of 10 cm. In order to control the temperature of the simulator block in a water bath an angle plate of stainless steel was mounted at two opposite sides, they can be bolted to the walls of the water bath that the simulator block is embedded in the water. On the bottom of the block there is a bore for the model liquid supply, at the front of the block the bore for the pressure measurement is located. The aluminum block is heated to 35-37° C. by the water bath to simulate the skin temperature.

The milled slot is hereinafter referred to as simulator chamber. This is dosed air-tight by means of a thin polymer film which is self-adhesive. For applying pressure a conventional device is in the form of a commercially available so-called T.R.A.C. pad is adhered to the film.

The vacuum pump for regulating the pressure in the simulator chamber is a PTFE diaphragm pump (model V-700, Büchi).

The pressure is measured with a commercially available differential pressure gauge.

The model fluid is conveyed from the storage vessel into the simulator chamber via a commercially available peristaltic pump, recording of the pressure in the simulator chamber is carried out on the PC over the pressure gauge software.

The collecting vessel for the model fluid is permanently balanced on a precision balance (CP 4202 S. Sartorius) to define the suction flow, recording of the data is carried out on the PC by Sarto Collect software from Sartorius.

2. Testing Method 2.1 Test Phase of the Wound Simulator

For the general function check the test facility was started without sample, solely equipped with as aluminum washer as a filler and a Duran glass frit for the uniform distribution of the model liquid in the chamber. Thus a statement could be made in how far the stability of the applied vacuum in the chamber is affected by the filling material.

2.2 Comparative Test with Conventional Wound Dressings

In the second step of the test phase, a conventional, in the vacuum therapy well-established wound dressing on the basis of a PU foam (V.A.C GranuFoam) of the company KCI® and a conventional gauze of the company Kalff® was examined. Further measurements were carried out with conventional wound treatment materials based on porous freeze-dried collagen materials (Matristypt®) from the company Dr. Suwelack Skin & Health Care AG, which are one-piece (non-layered), non-perforated sponge-like materials.

Therefore an albumin solution (4.04 g of bovine serum albumin from Prolabo in 100 mL of 0.9% sodium chloride solution), having a viscosity of 20 mPas was used as a model liquid. In the next step, the albumin model liquid was adjusted to a viscosity of about 100 mPas, by preparing and testing a variety of solutions for adjusting the viscosity, consisting of xanthan gum, hyaluronic acid or Carbopol Ultrez 21 (polyacrylic acid).

2.3 Experiments with Wound Treatment Materials According to the Present Invention Several perforated biomatrix layers were examined in the wound simulator with respect to their suitability to form the wound treatment materials according to the present invention as well as wound treatment materials formed of such biomatrix layers selected from Example 1.

3. Results 3.1 Test Run without Wound Dressing

FIG. 8 shows an example of the recording data from the internal pressure of the chamber and the amounts of conveyed and drained model fluid over a period of 345 min. It can be seen that the measured internal pressure with an average value of 117 mmHg deviates only slightly from the set pressure. The curves look similar for the previous test runs with the model fluids albumin, xanthan and hyaluronic acid. As an important statement it is apparent that for the following test runs with the respective wound dressings no influence on the internal pressure of the chamber or the fluid transport is effected from the filler materials (aluminum washer, glass frit).

3.2 Conventional Materials

FIGS. 9, 10 and 11 show the results of the examination of conventional wound dressings made of PU foam, gauze and collagen sponge in the wound simulator. When testing the collagen sponge, a large pressure drop was measured. The collagen blocks the transport of the model liquid and prevents the establishment of a constant pressure in the internal simulator chamber. The PU foam shows a constant pressure of 120 mmHg (average) over the entire measuring time of 795 min at an applied negative pressure of 125 mmHg and also the liquid transport is constant with a slight decrease, the average flow is 0.13 ml/min. The gauze as well as the polyurethane foam shows a constant vacuum in the chamber over the measuring time of 1160 min. With an applied negative pressure of 125 mmHg the average pressure is 124 mmHg. The fluctuations result from the pump type. The liquid transport is uniform over the entire term.

3.3 Wound Treatment Materials According to the Present Invention

FIG. 12 shows an example of the recording data from the internal pressure of the chamber and the amounts of conveyed and drained model fluid over a period of 420 min when using a perforated collagen biomatrix layer according to Example 1 Nr.1d (freeze-dried collagen crosslinked with epoxide (5%)).

It can be seen that the vacuum in the simulator chamber compared to the one-piece, non-perforated conventional collagen material has improved substantially. With an average of 85 mmHg at applied 125 mmHg, however, a deviation of 40 mmHg has been detected. Compared with the PU foam, this has to be assessed as poor and in need of optimization. The fluid transport is comparable to the behavior of the PU foam and has thus greatly improved compared to conventional collagen material.

FIG. 13 shows the results of Example 1 according to biomatrix layer No. 1a.

It becomes apparent that the vacuum in the simulator chamber has adjusted to the applied negative pressure of the pump. When negative pressure of 125 mmHg is applied an average of 102 mmHg over the measurement period of 420 min was measured. The pressure differences could thus be reduced from 40 mmHg to 27 mmHg. This results from the fact that by punching the collagen sheets channels exist that allow establishment of a uniform negative pressure and at the same time fluid transport.

FIGS. 14 and 15 show the results of materials according to Example No. 1 6a and 6b.

It is found that the geometry of the holes does not play a substantial role. It is important that continuous channels are present in the wound dressing, and that these are not blocked by any displacement of the wound dressing.

Also the variation of the total thickness of the wound treatment material to about 8 mm has no significant effect on the negative pressure in the simulator chamber and the transport of the model liquid.

EXPLANATION OF THE FIGURES

FIGS. 1 to 15 illustrate examples of the object of the present invention and illustrate various possible designs and embodiments of the wound treatment material according to the invention or of the perforated biomatrix layers forming the same.

FIG. 1 shows an exemplary embodiment of a perforated biomatrix layer with round or circular perforations.

FIG. 2 shows an exemplary embodiment of a perforated biomatrix layer with triangular perforations (side length of 4 mm).

FIG. 3 shows an exemplary embodiment of a perforated biomatrix layer with triangular perforations (side length of 8 mm).

FIG. 5 shows an exemplary embodiment of a wound treatment material of the invention composed of two perforated biomatrix layers with different perforation pattern.

FIG. 7 shows an exemplary embodiment with connecting means in the form of flaps and loops formed in the biomatrix layers.

FIG. 8 shows the result of the test run in the wound simulator without wound dressing.

FIG. 9 shows the result of a conventional PU foam wound dressing in the wound simulator.

FIG. 10 shows the result of a conventional collagen sponge wound dressing in the wound simulator.

FIG. 11 shows the result of a conventional gauze wound dressing in the wound simulator.

FIG. 12 shows the result of a wound dressing in the wound simulator wherein two exemplary embodiments of perforated biomatrix layers with round or circular perforations but without connecting means were piled and tested.

FIG. 13 shows the result of an exemplary embodiment of a perforated biomatrix layer with round or circular perforations in the wound simulator.

FIG. 14 shows the result of a wound dressing according to the present invention in the wound simulator FIG. 15 shows the result of a wound dressing according to the present invention in the wound simulator.

In FIG. 7 the reference signs have the following meaning:
1 biomatrix layer
2 loop formed from the biomatrix material
3 flap formed from the biomatrix material
4 perforation
5 wound treatment material formed from two biomatrix layers connected by loops and flaps

Figure 1:
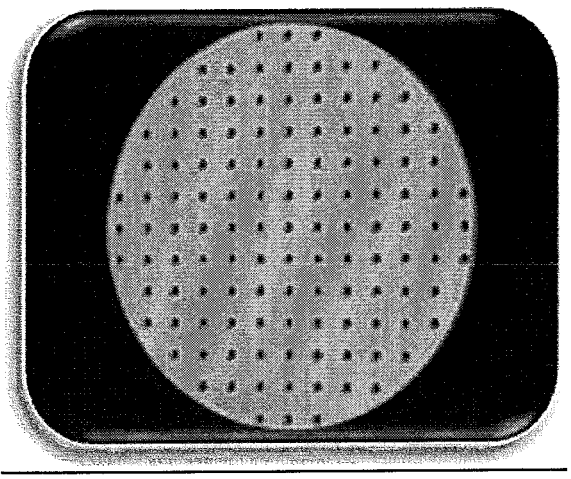
Figure 2:
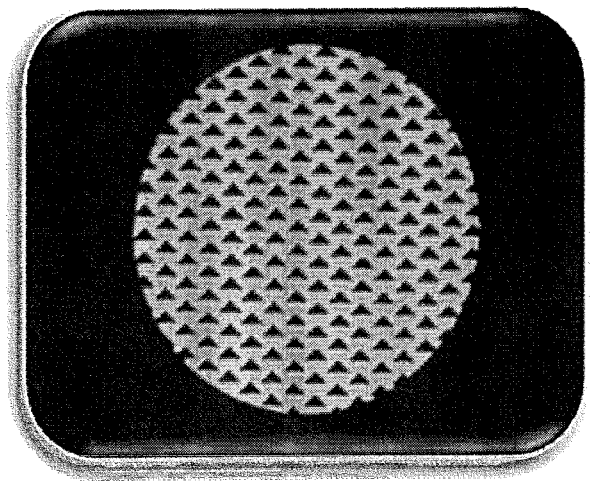
Figure 3:
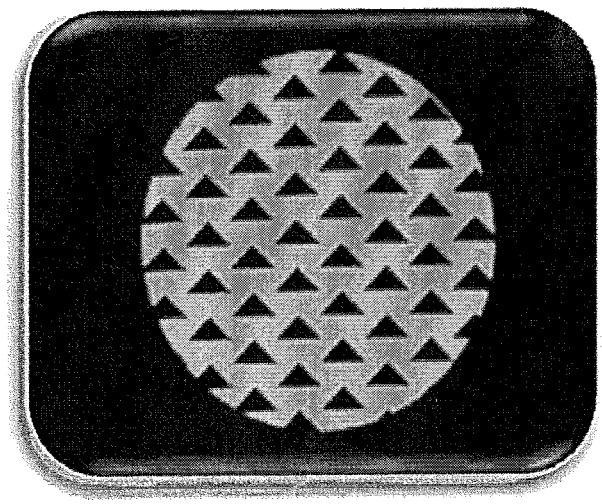
Figure 4A:
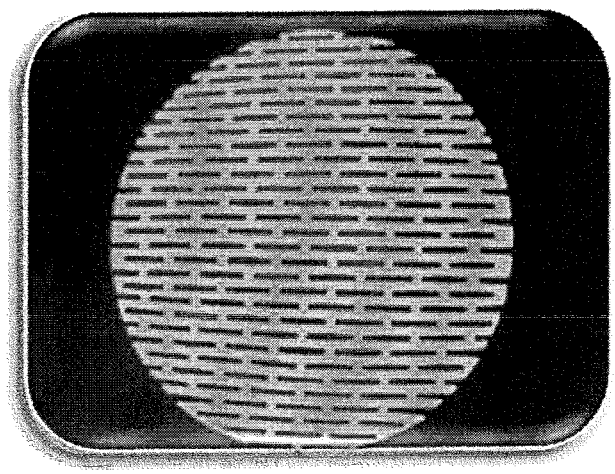
FIG. 4a shows an exemplary embodiment of a perforated biomatrix layer with rectangular or slot-shaped perforations in the pattern of a brick bond.
Figure 4B:
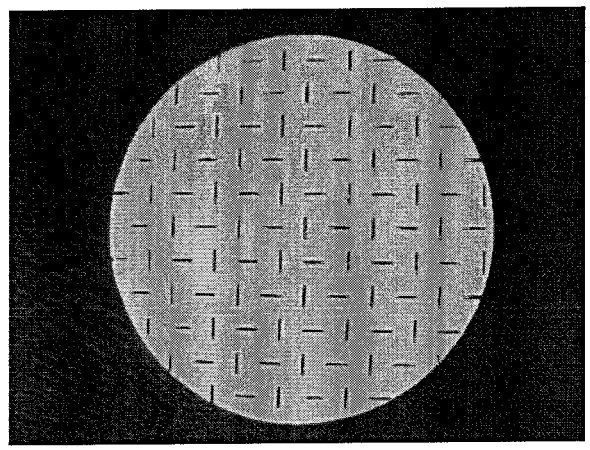
FIG. 4b shows an exemplary embodiment of a perforated biomatrix layer with slot-shaped perforations each 90° offset.
Figure 4C:
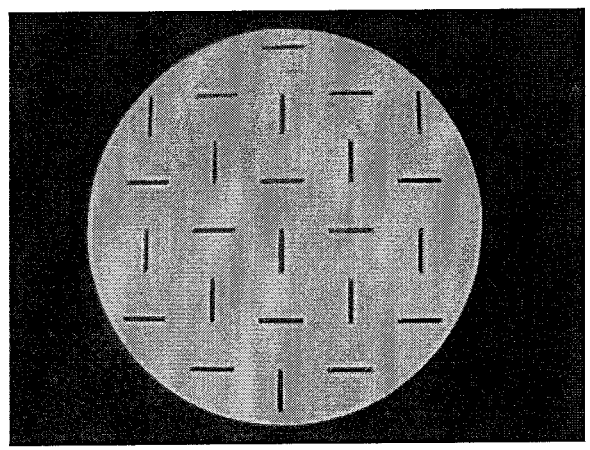
FIG. 4c shows an exemplary embodiment of a perforated biomatrix layer with slot-shaped perforations each 90° offset.
Figure 4D:
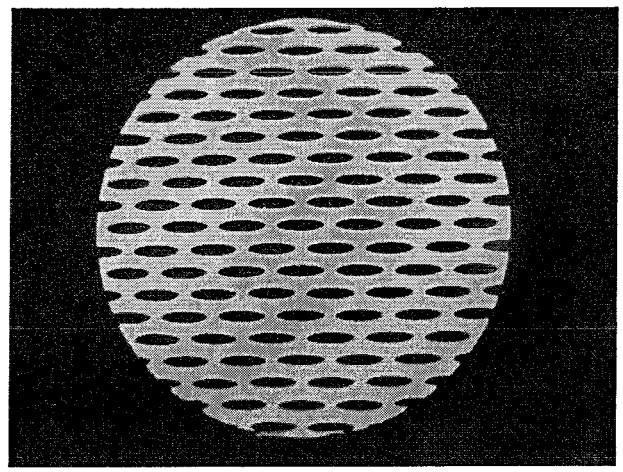
FIG. 4d shows an exemplary embodiment of a perforated biomatrix layer with elliptical or elongated oval perforations.
Figure 5:
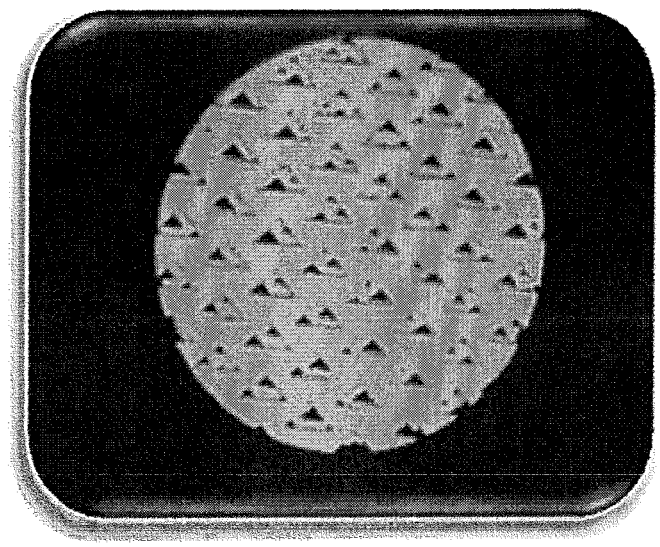
Figure 6A:
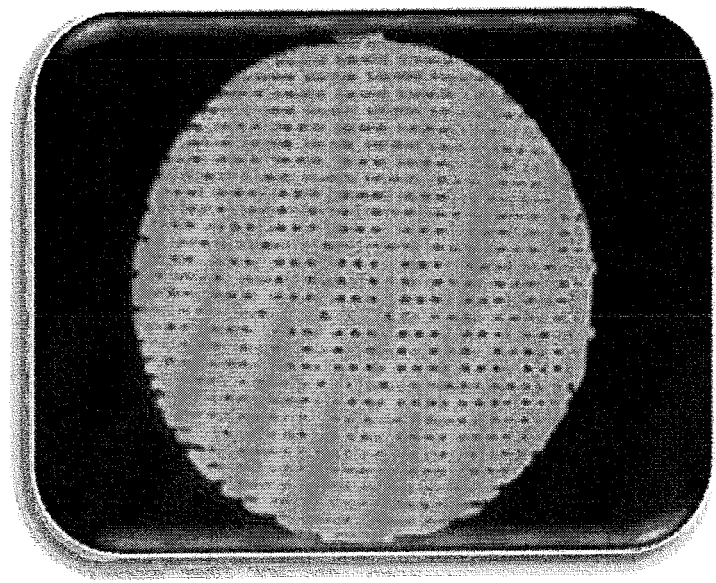
FIG. 6a shows an exemplary embodiment of a wound treatment material according to the invention composed of four perforated biomatrix layers with different perforation pattern.
Figure 6B:
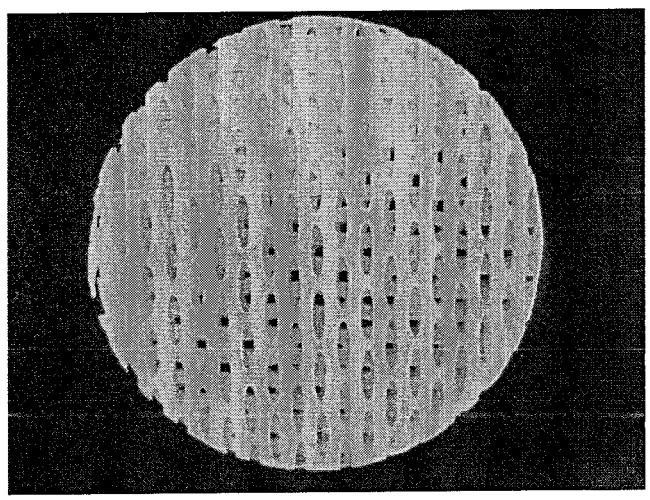
FIG. 6b shows an exemplary embodiment of a wound treatment material of the invention composed of two perforated biomatrix layers each with elliptical or elongated oval perforations.
Figure 7:
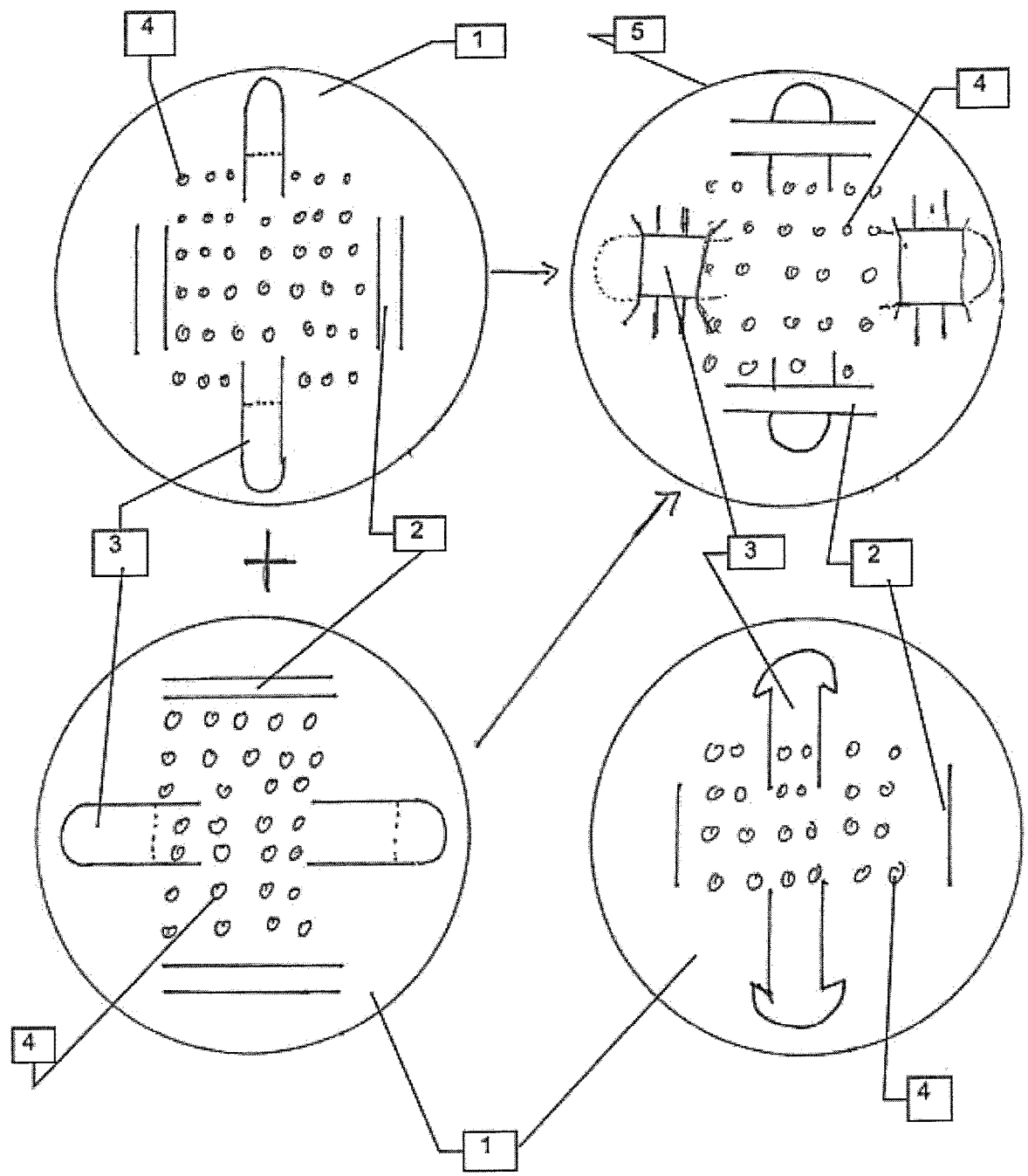
Figure 8:
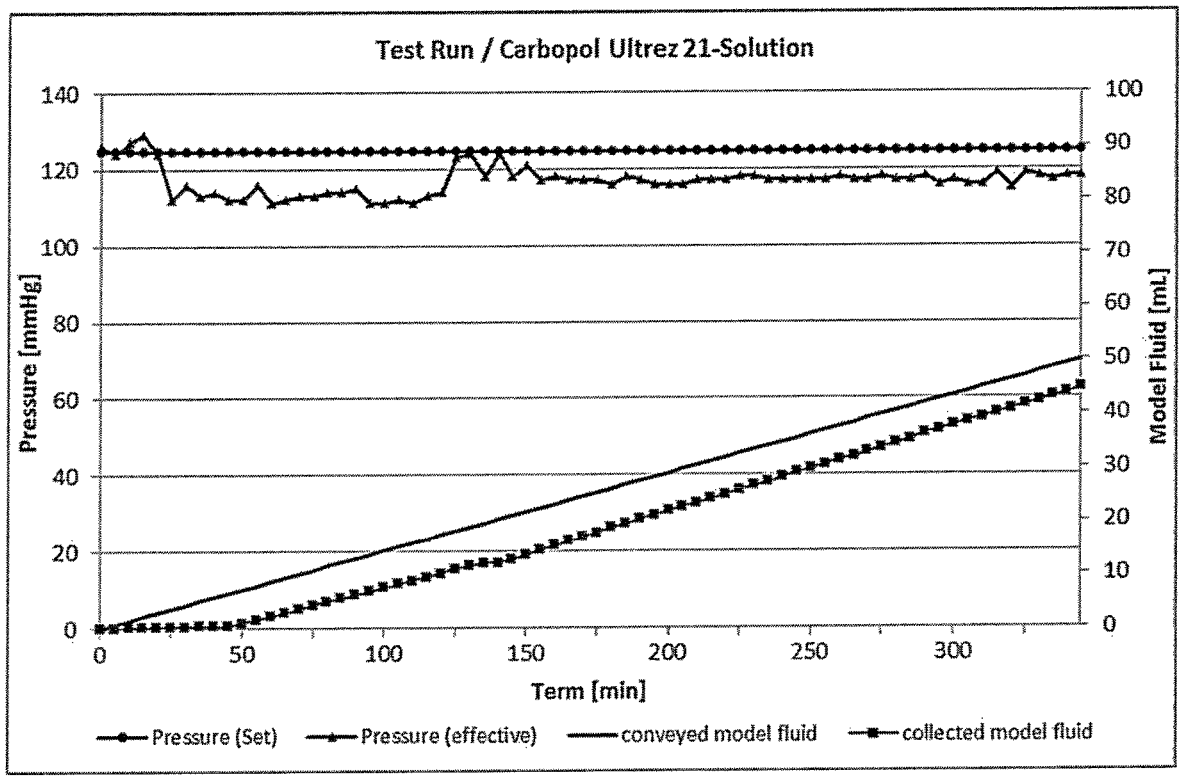
Figure 9:
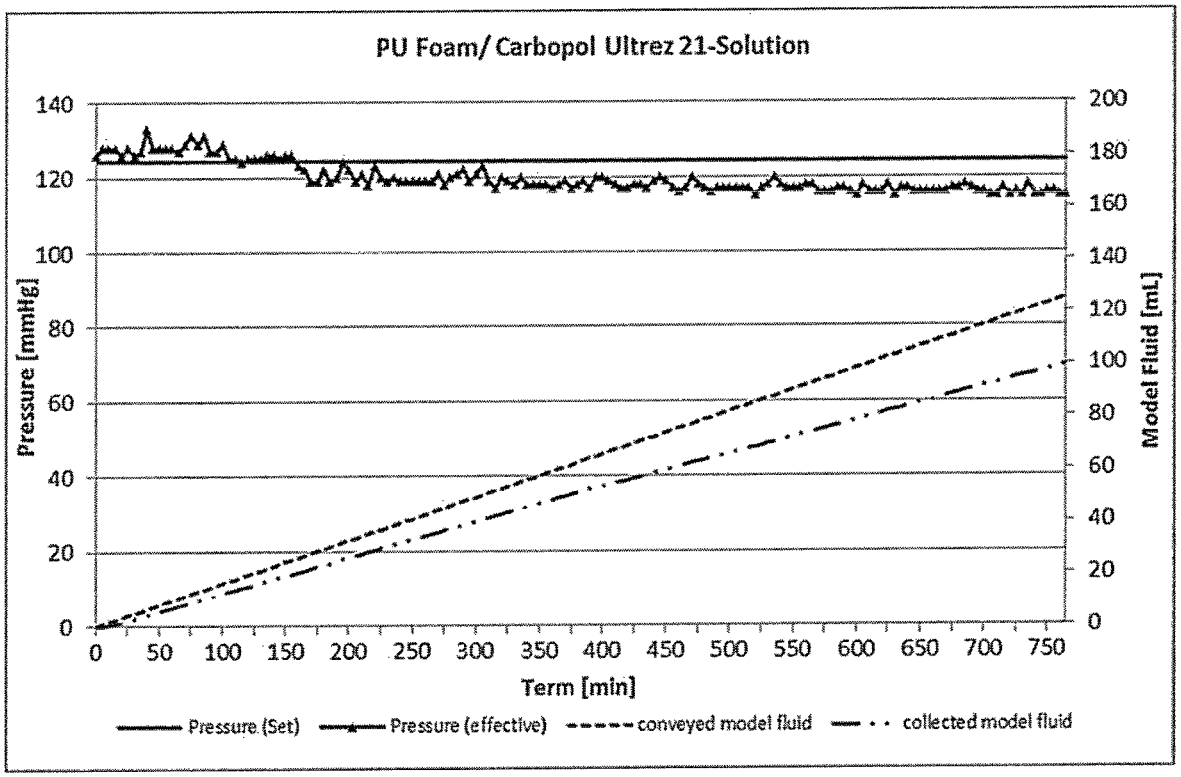
Figure 10:
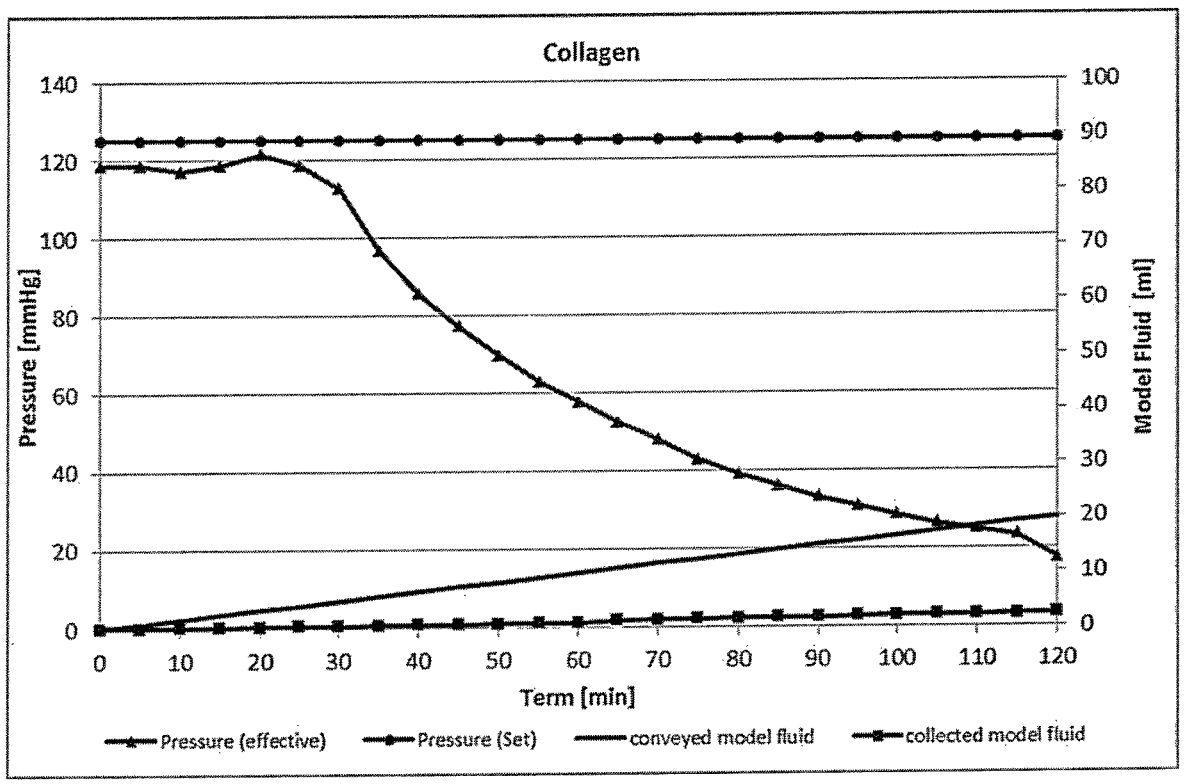
Figure 11:
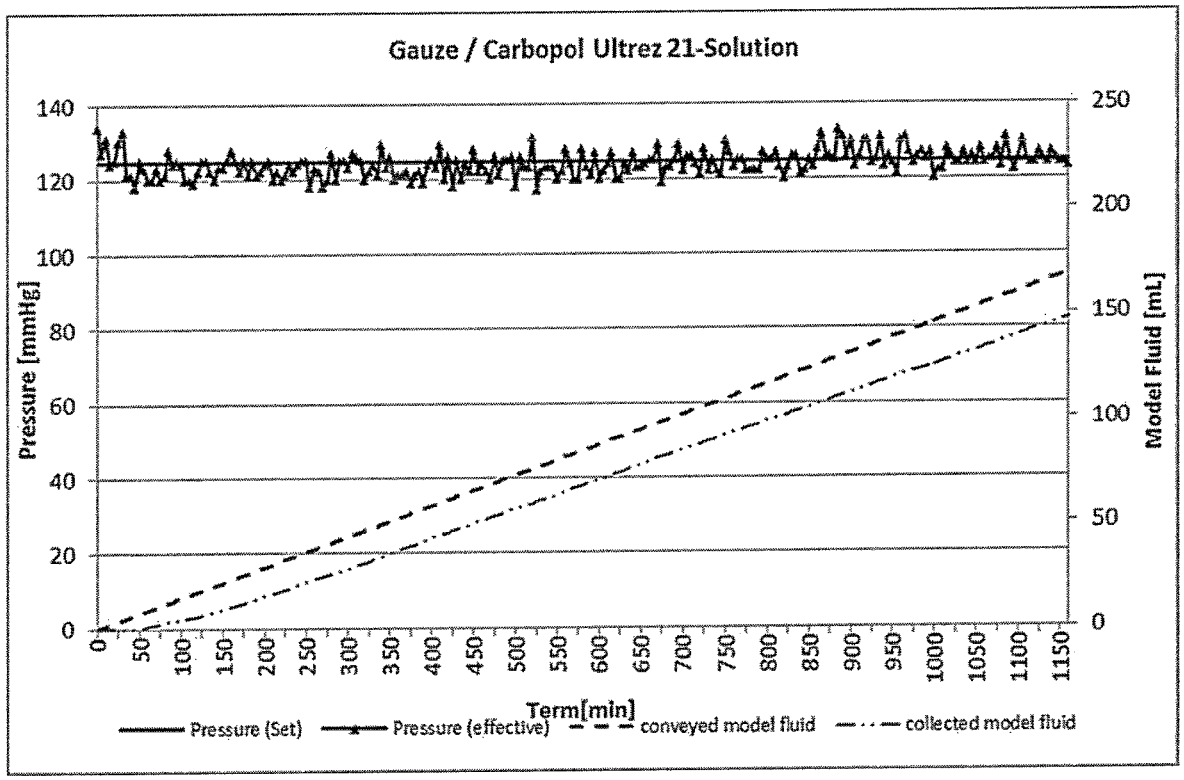
Figure 12:
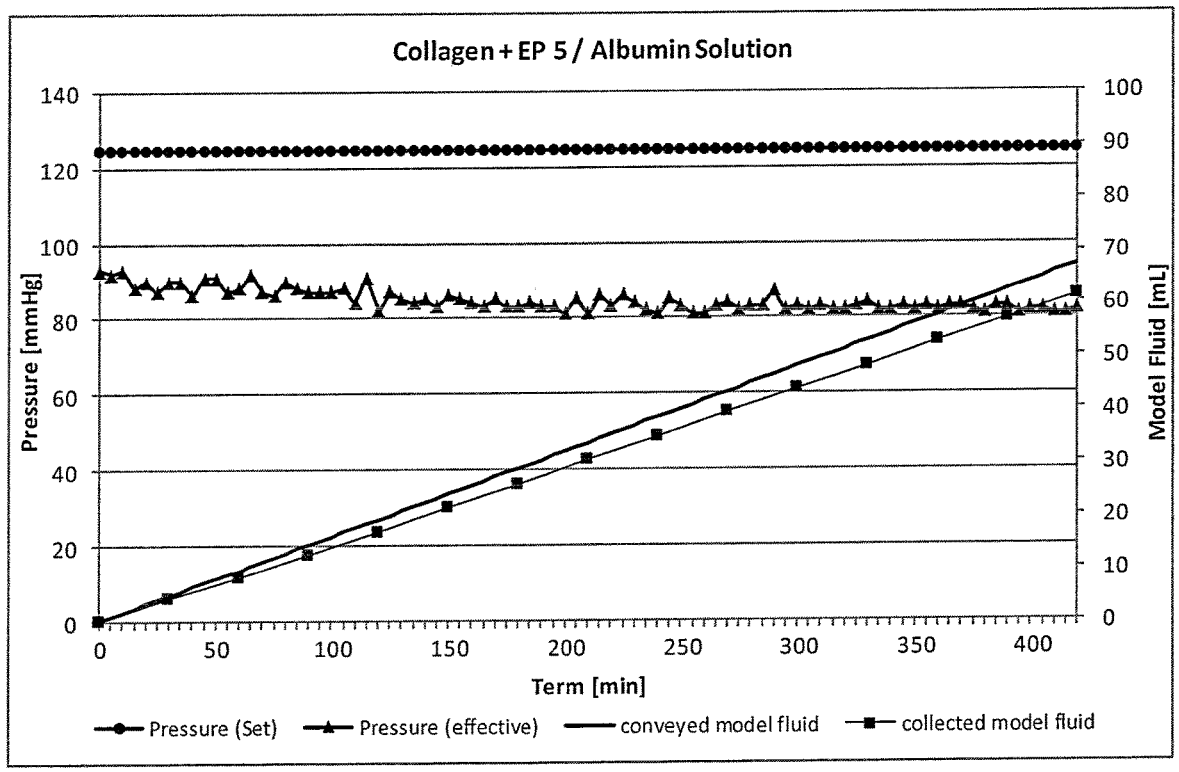
Figure 13:
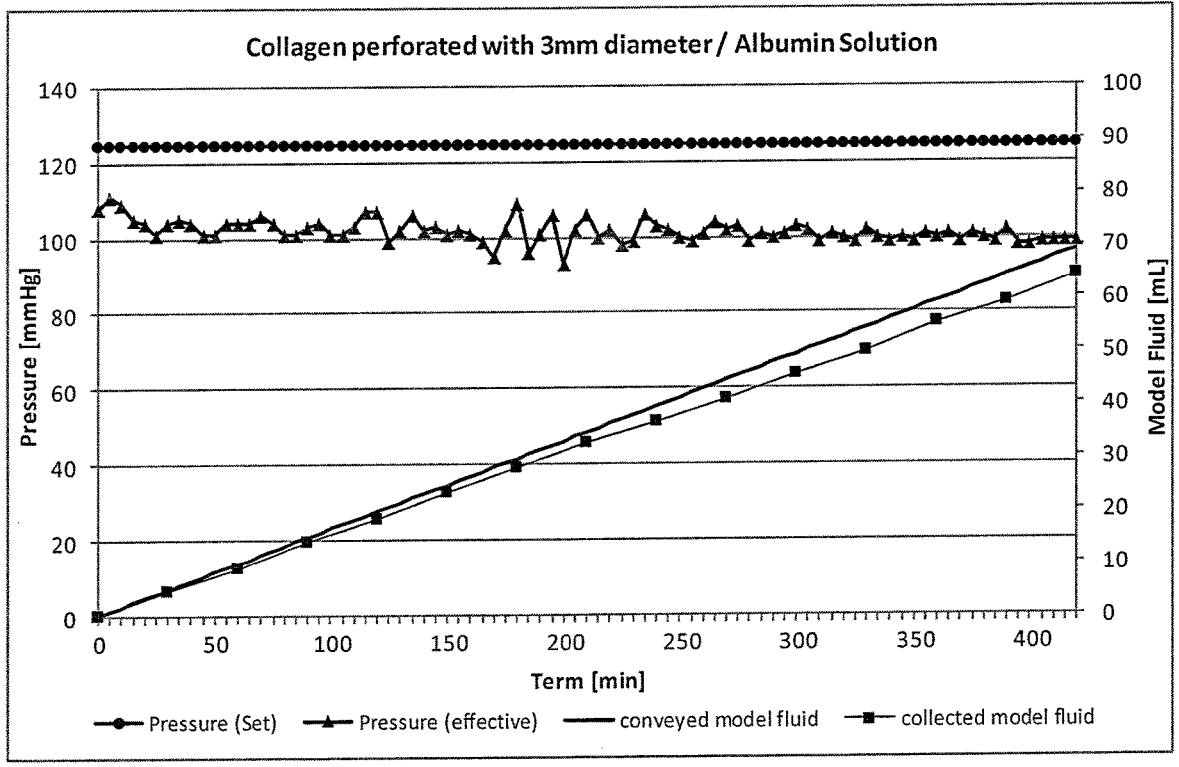
Figure 14:
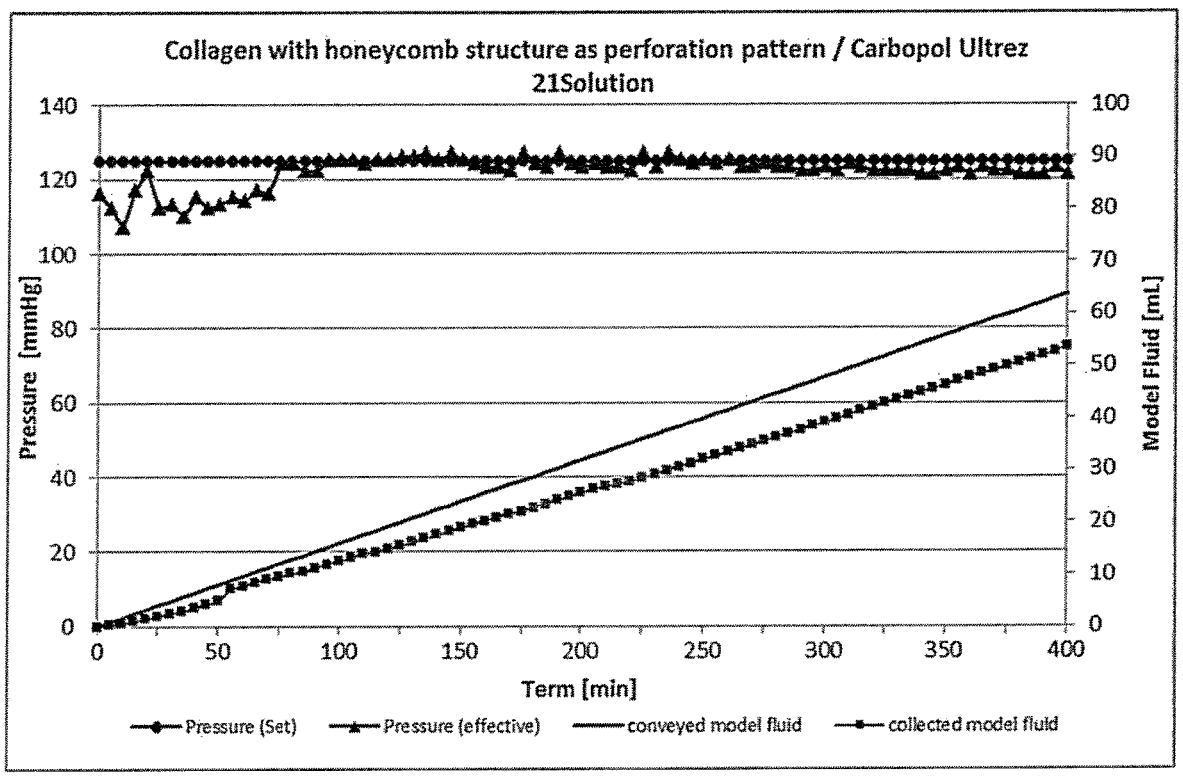
Figure 15:
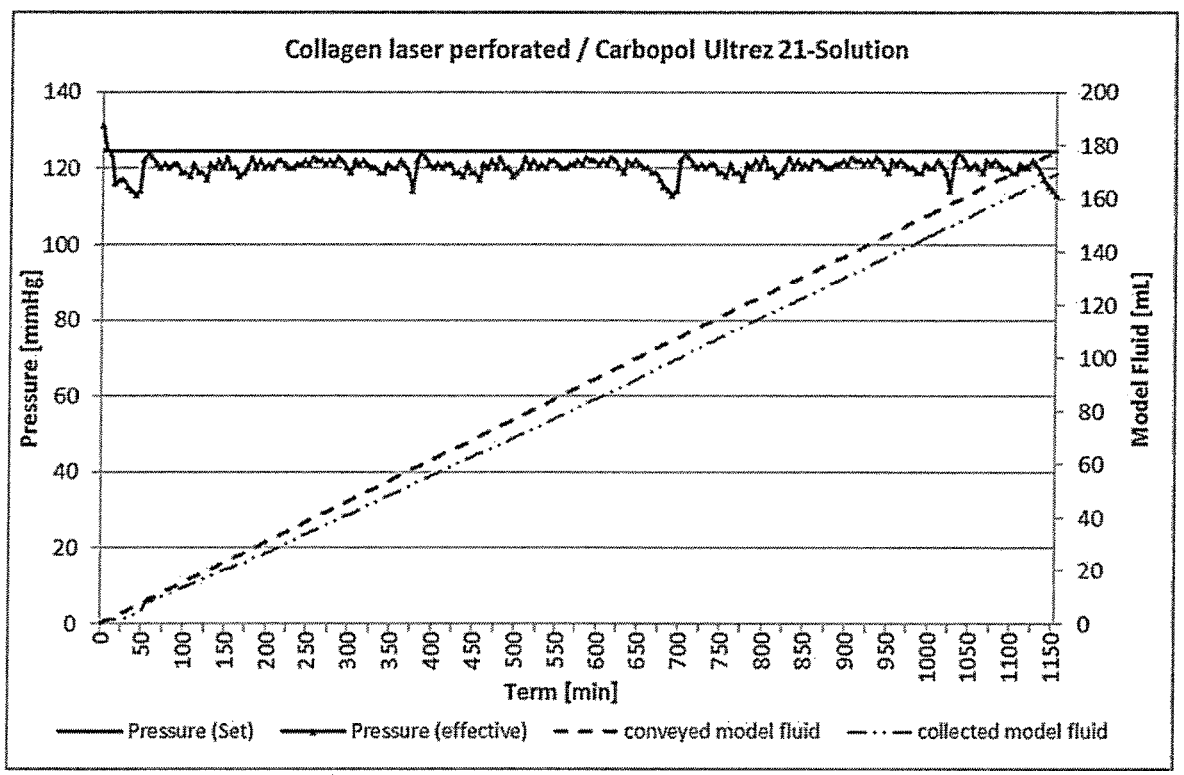

The invention claimed is:
1. A wound treatment material comprising at least two perforated biomatrix layers which are interconnected by a connecting agent,
  wherein the connecting agent is soluble in water or physiological environment and separable from at least one of the at least two perforated biomatrix layers and is selected from the group consisting of water soluble adhesives, physiologically acceptable spray adhesives, gelatin, and chitosan,
  wherein the at least two perforated biomatrix layers have perforations which are in slot form or in rectangular form offset relative to one another by 90°
  and wherein the at least two perforated biomatrix layers are formed from structure-forming natural polymers selected from the group consisting of animal derived hydrocolloids and plant derived hydrocolloids and mixtures thereof having a fine-porous sponge-like structure wherein an amount of the structure-forming natural polymers in the at least two perforated biomatrix layers is below about 70% by weight,
  wherein the at least two perforated biomatrix layers are obtained by a method comprising the steps:
  (a) preparing an aqueous suspension or solution of at least one structure-forming natural polymer;
  (b) pouring the aqueous suspension or solution into a mold;
  (c) drying the aqueous suspension or solution of step (b) to obtain a porous molded body;

(d) cutting the porous molded body obtained in step (c) into at least two biomatrix layers; and (e) perforating the at least two biomatrix layers;

wherein drying in step (c) comprises freeze-drying.

2. The wound treatment material according to claim 1, wherein the at least two perforated biomatrix layers are connected to each other in a way that continuous perforations throughout a total thickness of the wound treatment material are present.

3. The wound treatment material according to claim 1, wherein the structure-forming natural polymers are selected from the group consisting of collagens, polysaccharides, alginates, and combinations thereof.

4. The wound treatment material according to claim 1, wherein the at least two perforated biomatrix layers further comprise at least one of an active substance and an auxiliary substance.

5. The wound treatment material according to claim 1, wherein the at least two perforated biomatrix layers further comprise an active substance selected from the group consisting of hemostatic agents and wound treatment agents.

6. The wound treatment material according to claim 1, wherein at least one of (a) the at least two perforated biomatrix layers are the same or different, and (b) the at least two perforated biomatrix layers comprise perforations that are the same or different.

7. The wound treatment material according to claim 1, wherein the at least two perforated biomatrix layers have a thickness that is the same or different and are each up to 10 mm each.

8. The wound treatment material according to claim 1, wherein a total thickness of the at least two perforated biomatrix layers is at least 2 mm.

9. The wound treatment material according to claim 1, wherein the at least two perforated biomatrix layers are arranged upon one another such that even upon dissolution of the connecting agent and shifting of the at least two perforated biomatrix layers relative to one another, continuous perforations throughout the wound treatment material are retained.

10. A wound treatment material according to claim 1, further comprising one or more cover layers of a synthetic or semi-synthetic wound treatment material.

11. A wound treatment material according to claim 1 for use as at least one of (a) a hemostatic agent, (b) a treatment of at least one of (i) acute, (ii) chronic and (iii) exuding wounds, (c) an implant and (d) use in a vacuum-assisted wound treatment therapy.

12. The wound treatment material of claim 1, wherein the amount of the structure-forming natural polymers in the at least two perforated biomatrix layers is below about 60% by weight.

13. The wound treatment material of claim 1, wherein the amount of the structure-forming natural polymers in the at least two perforated biomatrix layers is below about 50% by weight.

14. A method for preparing a wound treatment material according to claim 1, comprising the steps of:

applying an adhesive to at least one biomatrix layer forming an adhesive coated first biomatrix layer and applying at least one additional biomatrix layer on the adhesive coated first biomatrix layer to give a desired total thickness of the wound treatment material, and perforation of the adhesive coated first biomatrix layer and at least one additional biomatrix layer which are interconnected by a connecting agent, wherein the connecting agent is soluble in water or physiological environment and separable from at least one of the adhesive coated first biomatrix layer and at least one additional biomatrix layer and is selected from the group consisting of water soluble adhesives, physiologically acceptable spray adhesives, gelatin, and chitosan, or perforation of the at least two perforated biomatrix layers, applying an adhesive to at least one of the at least two perforated biomatrix layers forming an adhesive coated first biomatrix layer and applying at least one additional perforated biomatrix layer on the adhesive coated first biomatrix layer to give a desired total thickness of the wound treatment material, wherein the at least two perforated biomatrix layers are arranged to form continuous perforations throughout the desired total thickness of the wound treatment material upon dissolution of the adhesive.

15. A wound treatment agent comprising a wound treatment material according to claim 1 together with a vacuum-tight cover sheet.

* * * * *